United States Patent [19]

Kridl et al.

[11] Patent Number: 5,420,034
[45] Date of Patent: * May 30, 1995

US005420034A

[54] SEED-SPECIFIC TRANSCRIPTIONAL REGULATION

[75] Inventors: Jean C. Kridl; Vic C. Knauf, both of Davis, Calif.

[73] Assignee: Calgene, Inc., Davis, Calif.

[ * ] Notice: The portion of the term of this patent subsequent to May 5, 2009 has been disclaimed.

[21] Appl. No.: 742,834

[22] Filed: Aug. 8, 1991

Related U.S. Application Data

[63] Continuation of Ser. No. 550,804, Jul. 9, 1990, abandoned, which is a continuation-in-part of Ser. No. 147,781, Jan. 25, 1988, abandoned, which is a continuation-in-part of Ser. No. 78,538, Jul. 28, 1987, abandoned, which is a continuation-in-part of Ser. No. 891,529, Jul. 31, 1986, abandoned.

[51] Int. Cl.$^6$ .................. C12N 5/00; C12N 15/05
[52] U.S. Cl. .................. 435/240.4; 435/320.1; 536/24.1; 935/22; 935/30; 935/67
[58] Field of Search .................. 536/27, 24.1; 435/240.4, 320.1; 800/205; 935/22, 30, 67

[56] References Cited

U.S. PATENT DOCUMENTS 4,769,061  9/1988  Comai .................. 71/86
4,886,753  12/1989  Marcher et al. .................. 435/172.3

FOREIGN PATENT DOCUMENTS 142924    5/1985   European Pat. Off. ...... C12N 15/00
0193259   3/1986   European Pat. Off. .......... 435/172.1
85/04899  11/1985  WIPO .................. C12N 15/00
87.07299  12/1987  WIPO .................. C12N 15/00

OTHER PUBLICATIONS

Goodman et al. Science vol. 236 pp. 48–54 (1987).
Barton et al. (1987) Plant Physiology. 85 pp. 1103–1109.
Crouch et al. *Planta*, "Development and Storage—Protein Synthesis in 'Brassica Napus' L. Embryos In Vivo and In Vitro", vol. 153, pp. 64–74 (1981).
Crouch et al. *Journal of Molecular and Applied Genetics*, "cDNA Clones for 'Brassica Napus' Seed Storage Proteins: Evidence from Nucleotide Sequence Analysis that Both Subunits of Napin Are Cleaved From a Precursor Polypeptide", vol. 2, pp. 273–283 (1983).
Crouch et al. Molecular Form and Function of the Plant Genome, "Storage Protein mRNA Levels Can Be Regulated by Abscisic Acid in Brassica Embryos", pp. 555–566.
Simon et al. *Plant Molecular Biology*, "Nucleotide Sequence of a cDNAP Clone of 'Brassic Napus' 12S Storage Protein Shows Homology with Legumin from 'Pisum Sativum'" vol. 5, pp. 191–201 (1985).
Scofield et al. *Journal of Biological Chemistry*, "Nucleotide Sequence of a Member of the Napin Storage Protein Family From 'Brassica Napus'" vol. 262 No. 25, pp. 12202–12208, (1987).
Rose et al. *Nucleic Acids Research*, "The Nucleotide of a cDNA Clone Encoding Acyl Carrier Protein (ACP) from Brassica Campestris Seeds", vol. 15, No. 17, p. 7197 (1987).
Scherer et al. *Plant Molecular Biology*, "Isolation of a cDNA Clone for the Acyl Carrier Protein-I of Spinach", PLAN 0043, pp. 1–8 (1987).
Beachy et al. *EMBO Journal*, "Accumulation and Assembly of Soybean (Beta)-Conglycinini in seeds of Transformed Petunia Plants", vol. 4, No. 12, pp. 3047–3053, (1985).

(List continued on next page.)

Primary Examiner—Gary Benzion
Attorney, Agent, or Firm—Barbara Rae-Venter

[57] ABSTRACT

Nucleic acid sequences and methods for their use are provided which provide for seed-specific transcription, in order to modulate or modify expression in seed, particularly embryo cells. Transcriptional initiation regions are identified and isolated from plant cells such as seed embryo and seed coat and used to prepare expression cassettes which may then be transformed into plant cells for seed-specific transcription. The method finds particular use in conjunction with modifying fatty acid production in seed tissue.

11 Claims, 27 Drawing Sheets

OTHER PUBLICATIONS

Sengupta-Gopalan et al. *Proc. Natl. Acad. Sci. USA*, "Developmentally Regulated Expression of the Bean (Beta)-Phaseolin Gene in Tobacco Seed", vol. 82, pp. 3320-3324. (May, 1985).

Greenwood et al. *Plant Physiol.*, "Correct Targeting of the Bean Storage Protein Phaseolin in the Seeds of Transformed Tobacco", vol. 79, pp. 65-71, (1985).

Chen et al. *Proc. Natl. Acad. Sci.*, "Functional Analysis of Regulatory Elements in a Plant Embryo-Specific Gene", vol. 83, pp. 8560-8564, (1986).

Eckes et al. *Mol. Gen. Genet.*, "Isolation and Characterization of a Light-Inducible, Organ-Specific Gene from Potato and Analysis of its Expression After Tagging and Transfer into Tobacco and Potato Shoots"; vol. 205, pp. 14-22 (1986).

Fluhr et al. *Science*, "Organ-Specific and Light-Induced Expression of Plant Genes", vol. 232, pp. 1106-1112, (1985).

Padgett, et al. *Ann. Rev. Biochem.*, "Splicing of Messenger RNA Precursors", vol. 55, pp. 1119-1150, (1986).

Vasil (1988) *Biotechnology*, 6:397-402.

Murray et al. (1983) *Z. Pflanzenphysiol.*, 110(1):7-16.

Facciotti et al. (1985) *Biotechnology* 3(3):241-246.

Ohlrogee et al. (1986) *CA, 105, p164 No. 55584k (1986)*.

Kuo et al., (1984) *Archives of Biochem. and Biophysics*, 234(1):290-296.

Willmitzer (1988) *Transgenics*, 4:13-18.

Goldberg et al. (1989) *Cell*, 56:149-160.

Knauf, J. Amer. Chem. Soc. 64(5) May 1987, abstracts from meeting, p. 633 No. 55.

Radke et al., *Commonwealth Agricultural Bureau*, abst. No. CAB 881669878 (1986).

Scofield et al., *J. Cell Biochem. Suppl.*, part 9C, p. 222 abst. No. 1695 (1985).

"The Use of Transgenic Plants to Study Plant Gene Expression", by Lothar Willmitzer, *Trends in Genetics*, (1988) 4:13-18.

"Regulation of Gene Expression During Plant Embryogenesis", by Robert B. Goldberg, et al., *Cell*, (1989) 56:149-160.

pGN1

```
      TaqI                                   HindIII
                                             AluI            TaqI
  1 GTCGAGGCAGTCACTAACATGAAGTTTGACGAGGAGCCCAACTATGGAAGCTTATTTCTCTTTTCGAT   69
    3                                        50  52                  66

HhaI XbaI                          SacI
                                                 AluI
 70 ACTCTAATTGAGCCGTGCGCTCTATCTAGACCAATTAGAATTGATGGAGCTCTAAAGGTTGCTGGCTGT  138
              89   95                            119 121

NdeI                                          NdeI
139 TTTCTTGTTCATATGATTAACTTCTAAACTTGTGTATAAATATTCTCTGAAAGTGCTTCTTTTGGCATA  207
                    150                                                206

208 TGTAGGTTGGGCAAAAACGAGAAGAGATTGCTTCTCAATTTGGAAGATGATGAACAGCCGAAGAAGAAAA  276

Sau3AI
                                    DdeI
277 TAAGAATAGGCAGTCCTGCTACTCAATGGATCTCAGTCTATAACGGTCGTCGTCCCATGAAACAGAGGT  345
                                    305 309
```

FIG. 1A

```
                                                          Sau3AI     AluI
                                                          ─┬──       ─┬──
                                                          1156       1166
1105 CATAGGAGGTGGGAGAATGGGTATAGAATAACATCAATGGCAGCAACTGCGGATCAAGCAGCTTTCATA 1173

HinfI
                          ─┬──
                          1216
1174 TTAAGCATACCAAAGCGTAAGATGGTGATGAAACTCAAGAGACTCTCCGCACCACCGCCTTTCCAAGT 1242

ScaI             AluI                    Sau3AI
     RsaI             ─┬──                    ─┬──
     ─┬──             1269                    1286
     1243
     1243
1243 ACTCATGTCAAGGTTGGTTTCTTTAGCTTTGAACACAGATTTGGATCTTTTTGTTTTGTTTCCATATAC 1311

DdeI                                              HinfI    RsaI
     AvaII   AluI                                          ─┬──     ─┬──
     ─┬──    ─┬──                                          1368     1375
     1316    1326
     1320
1312 ATAGGACCTGAGAGCTTTTGGTTGAATTTTTTTTTTCAGGACAAATGGGCGAAGAATCTGTACATTG 1380

1381 CATCAATATGCTATGGCAGGACAGTGTGCTGATGATACACACTTAAGCATCATGTGTGTGTTAGAAAG 1449

MstII                                       Tth111I
              DdeI                                        ─┬──
              ─┬──                                        1514
              1472
              1472
1450 CCGAAGACAATTGGAGCGAGCCTCAGGTGTCGTCATAATACCAATCAAAGACGTAAAACCAGACGCAGTC 1518
```

FIG. 1D

```
                                                          RsaI
1519 TCTTTGGTTGAATGTGATGAAAGGGATGTGTCTTGGTATGTATGTACGAGTAACAAAGAGAAGATGCA 1587
                                                            1564

AluI  DraI                                    EcoRV
1588 ATTGAGTAGTAGAAAGATTTGAGAGCTTTTAAAGCCCCTCAAGTGTGCTTTTATCTTATTGATATC 1656
                 1613  1619                                      1654

DdeI
1657 ATCCATTTGCGTTGTTAATGCGTCTTTAGATATGTTTCTGTTTCTTCCTCAGTGTCTGAATATCTGAT 1725
                          1706

TaqI
                                                         HinfI
1726 AAGTGCAATGTGAGAAAGCCACACCAAATATTCAAATCTTATATTTTTAATAATGTCGAATCA 1794
                                                          1790
                                                         1788

HinfI
1795 CTCGGAGTTGCCACCTTCTGTGCCAATTGTGCTGAATCTATCACACTAAAAAAACATTTCTTCAAGGT 1863
                             1829

EcoRI
1864 AATGACTTGTGGACTATGTTCTGAATTCTCATTAAGTTTTTATTTTTGAAGTTTAAGTTTTTACCTTC 1932
            1887
```

FIG. 1E

Lambda CGN1-2
NCG-186 Linear          LENGTH = 4325

```
         Xhol                                              HindIII
         TaqI                                              AluI      TaqI
         AvaI                                              !         !
         !!!                                               !
  1 CTCGAGGCAGTCACTAACATGAAGTTTGACGAGGAGCCCAACTATGGGAAGCTTATTCTCTTTCGAT   69
       2 3                                            50 52          66
       2

HhaI XbaI                             SacI
              !    !                                AluI
              !    !                                !                    NdeI
                                                                         !
 70 ACTCTAATTGAGCCGTGCGCTCTATCTAGACCAATTAGAATTGATGGAGCTCTAAAGGTTGCTGGCTGT  138
          89   95                                       119
                                                          121

NdeI
     !
139 TTTCTTGTTCATATGATTAACTTCTAAACTTGTGTATAAATATTCTCTGAAAGTGCTTCTTTTGGCATA  207
                150                                                      206

208 TGTAGGTTGGGCAAAAACGAGGAAGATTGCTTCTCAATTTGGAAGAGAGGATGAACAGCCGAAGAAGAAAA  276
                  Sau3AI
                  DdeI
                  !
277 TAAGAATAGGCAGTCCTGCTACTCAATGGATCTCAGTCTATAACGGTCGTCGTCCCATGAAACAGAGGT  345
                                    305 309

EcoRV
                                                            !
346 AAAACATTTTTTGCATATACACTTTGAAAGTTCCTCACTAACTGTGTAATCTTTTGGTAGATATCACTA  414
                                                              408
```

```
                                Hincll
                                Hhal
                                Haelll
                                Ddel                              Haelll      Alul
                                BstEll                            |           |
                                Ball                              |           |
                                |||                439           469         481
                                438
                                439
                                439
                                440
                                438
415 CAATGTCGGAGAGACAA3GGCTGMNCANCATATACAAAAGGGAAATGAAGATGGCCTTTTGATTAGCTG 483

Alul                                      Hinfl
        |                                         |
       498                                       535
484 TGTAGCATCAGAGCTAATCTCTGGGCTCTCATCATGATGCTGGAACTGGATTCACTTCTCAAGTTTA 552

Mspl                                          Hinfl
     Hpall                                         |
     |                                            606
     564
     564
  Ddel
  |
553 TGAGTTGTCACCGGTCTTCCTACACAAGGTAATAATCAGTTGAAGCAATTAAGAATCAATTGATTGT 621

629
622 AGTAAACTAAGAAGAACTTACCTTATGTTTTCCCCGCAGGACTGGATTATGAACAATGGGAAAAGAAC 690

SacI
        Alul      Alul                             Alul
        |         |                                | |
       702       710                              729
                                                     731
691 TACTATATAAGCTCCATAGCTGGTTCAGATAACGGGAGCTCTTAGTTGTTATGTCAAAAGGTTAGTGT 759
```

```
760  TTAGTGAATAATAACTTATACCACAAGTCTTCATTGACTTATTTATATACTTGTTGTGAATTGCTAG 828
                                      Ddel         Hinfl
829  GAACTACTTATTCTCAGCAGTCATACAAGTGAGTGACTCATTCCGTTCAAGTGGATAAATAAGAAAT 897
              Xmnl                     842                865
                                                                              Taql
898  GGAAAGAAGATTTCATGTAACCTCCATGACAACTGCTGGTAATCGTTGGGGTGTGGTAATGTCGAGGA 966
                        908                                                961
           Sau3AI
           Bcll
967  ACTCTGGCTTCTCTGATCAGGTAGGTTTTTGTCTCTTATTGTCTGGTGTTTTATTTCCCCTGATAGT 1035
         981                    Alul            Rsal
         981
1036 CTAATATGATAAACTCTGCCGTTGTGAAAGGTGGTGGAGCTTGACTTTTTGTACCCAAGGCGATGGGATAC 1104
                                                      1074              1087
                                                Sau3AI    Alul
1105 ATAGGAGGTGGGAGAATGGGTATAGAATAACATCAATGGCAGCAACTGCGGATCAAGCAGCTTTCATAT 1173
                                                              1155      1165
                         Hinfl                                      Scal
                                                                    Rsal
1174 TAAGCATACCAAAGGCTAAGATGGTGGATGAAACTCAAGAGACTCTCCGACCACCGCCTTTCCAAGTA 1242
                                   1215                                  1242
                                                                          1242
```

FIG. 2C

```
                                    AluI        Sau3AI              DdeI
1243 CTCATGTCAAGGTTGGTTTCTTTAGCTTTGAACACAGATTTGGATCTTTTTGTTTGTTTCCATATACT 1311
                                      1268         1285                   1311

DdeI
     AvaI|  AluI                                          HinfI  RsaI
1312 TAGGACCTGAGAGCTTTTGGTTGATTTTTTTTTCAGGACAAATGGGCGAAGAATCTGTACATTGCATCA 1380
     1315 1319                                            1363  1370
          1325

1381 ATATGCTATGGCAGGACAGTGTGCTGAGTGCTGATACACACTTAAGCATCATGTGGAAAGCCAAAGACAATTGGAG 1449

HinfI
     DdeI
1450 CGAGACTCAGGGTCGTCTCATAATACCAATCAAAGACGTAAAACCAGACGCAACCTCTTTGGTTGAATGTA 1518
         1454
         1456

RsaI
1519 ATGAAAGGGATGTGTCTTGGTATGTATGTACGAATAACAAAAGAGAAGATGGAATTAGTAGTAGAAATA 1587
                                1548

AluI                                    EcoRV
1588 TTTGGGAGCTTTTTAAGCCCTTCAAGTGTGCTTTTATCTTATTGATATCTTATTGCGTTGTTTAA 1656
             1596                                    1635

XbaI                                 DdeI
1657 TGCGTCTCTAGATATGTTCCTATATCTTTCTCAGTGTCTGATAAGTGAAATGTGAGAAAACCATACCAA 1725
     1664                                 1687
```

FIG. 2D

```
                                    HinfI
                                     |-
1726 ACCAAAATATTCAAATCTTATTTTAATAATGTTGAATCACTCGGAGTTGCCACCTTCTGTGCCAATTG 1794

HinfI                                                    EcoRI
         |-                                                       |-
1795 TGCTGAATCTATCACACTAGAAAAAAACATTTCTTCAAGGTAATGACTTGTGGACTATGTTCTGAATTC 1863
                1800                                   1859

1864 TCATTAAGTTTTTATTTTCTGAAGTTTAAGTTTTTACCTTCTGTTTTGAAATATATCGTTCATAAGATG 1932
                                                          SphI
                                                          Sau3AI
                                                          |-
                 BstNI    AluI                           1973
                  |-       |-                            1971
1933 TCACGCCAGGACATGAGCTACACATCGCACATAGCATGCAGATCAGGACGATTGTCACTCACTTCAAA 2001
              1940      1950

DdeI   AluI       HhaI  NdeI NsiI    SphI       Sau3AI
          |-     |-         |-    |-   |-                 |-
2002 CACCTAAGAGCTTCTCTCACAGCGCACACATATGCATGCAATATTTACACGTGATCGCCATGCAA 2070
          2006 2012      2028  2036 2042                 2058
                                    2044

2071 ATCTCCATTCTCACCTATAAATTAGAGCCTCGGCTTCACTCTTTACTCAAACCAAAACTCATCACTACA 2139
                                  AluI
                                  |-
2140 GAACATACACAAATGGCGAACAAGCTCTTCCTCGTCTCGGCAACTCTCGCCTTGTTCTTCCTTCTCACC 2208
                     METAlaAsnLysLeuPheLeuValSerAlaThrLeuAlaLeuPhePheLeuLeuThr
                            2164
```

```
                                                                  Nael
                                                                  Mspl
                                                         Taql     Hpall
                                                         Sall      |    Haelll
                                                         Hincll    |     |
                                                         Accl      |     |
              Accl                                       | | |     |     |
              |                                                                                        2277
2209 AATGCCTCCGTCTACAGGACGGTTGTGGAAGTCGACGAAGATGATGCCACAAATCCAGCCGGCCCATTT
     AsnAlaSerValTyrArgThrValValGluValAspGluAspAspAlaThrAsnProAlaGlyProPhe
                2220                            2239                   2271
                                                2240            2268
                                                2241            2268
                                                                2269

HindIII
                                                        AluI
     Hinfl                                              | |
     |                                                                                                 2346
2278 AGGATTCCAAATGTAGGAAGGAGTTTCAGCAAGCAACAACCTGAAAAGCACAAGCTTGCCAACAATGGCTCCAC
     ArgIleProLysCysArgLysGluPheGlnGlnGlnGlnProGluLysHisLysLeuAlaAsnAsnGlySerThr
     2281                                                         2325
                                                                  2327

Mspl         AvalI  AluI  AvalI
                           Hpall        |      |     Taql
                           | |          |      |     |                                                 2415
2347 AAGCAGGCAATGCAGTCCGGTAGTGGTCCAAGCTCCGATGGTGAGTTTGATTTGAAGACGAC
     LysGlnAlaMetGlnSerGlySerGlyProSerSerAspGlyGluPheAspPheGluAspAsp
                       2364          2372  2379  2382
                       2364

Haelll
                   Apal
                   | |                                                                                 2484
2416 GTGGAGAACCAACAACAGGGCCCGCAGAGGCCACCGTGCTCCAGCAGTGCTGCAACGAGCTCCAC
     ValGluAsnGlnGlnGlnGlyProGlnArgProProValLeuGlnGlnCysCysAsnGluLeuHis
                  2436                    2449                          2479
                  2438                                                  2481

BstNI                                                         Hinfl  Sacl  Alul
     |                                                             |      |     |
                                                                                                       2553
2485 CAGGAAGAGCCACTTGCGTTTGCCCAACCTTGAAAGGAGCATCCAAAGCCGTTAAACAACAGATTCGA
     GlnGluGluProLeuCysValCysProThrLeuLysGluGluHisProLysProLeuAsnAsnArgSer
                                 2486                      2548     2551
```

```
                                                                                    BstNI
2554 CAACAACAGGGACAACAAATGCAGGGACAGCAGATGCAGCAAGTGATTAGCCGTATCTACCAGACCGCT 2622
      GlnGlnGlnGlyThrLysMETGlnGlyGlnGlnMETGlnGlnValIleSerArgIleTyrGlnThrAla
              AluI

2623 ACGCACTTACCTAGAGCTTGCAACATCAGGCAAGTAGCATTGCCCCTTCCAGAAGACCATGCCTGGG 2691
     ThrHisLeuProArgAlaCysAsnIleArgGlnValSerIleCysProPheGlnLysThrMETProGly 2688
                       HinfI                        XhoI        AccI
          MspI                                       TaqI
          HpaII                                      AvaI
     HaeIII  2639                                      2724
     ApaI                                              2725
2692 CCCGGGCTTCTACTAGATTCCAAACGAATATCCTCGAGAGTGTGTATACCACGGTGATATGAGTGTGGTT 2760
     ProGlyPheTyr               2707                        2736
      2692
      2694
      2694
      2694
            HincII
             2771
       AccI                              RsaI
2761 GTTGATGATGTATGTTAACACTACTAGTCATGGTGTGTTCCATAAATAATGTACTAATGTAATAAGAAC 2829
                                                          2813

2830 TACTCCGTAGACGGGTAATAAAAGAGAAGTTTTTTTTTTTACTCTTGCTACTTTCCTATAAAGTGATGAT 2898
          2838
                                                                    ScaI
                                                                    RsaI
2899 TAACAACAGATACACCAAAAGAAAACAATTAATCTATATTCACAATGAAGCAGTACTAGTCTATTGAA 2967
                                                                 2954
                                                                 2954
```

FIG. 2G

```
                                                                              Sau3AI
                                                                                |
2968 CATGTCAGATTTCTTTCTTTTCTAAATGTCTAATTAAGCCTTCAAGGCTAGTGATGATAAAAGATCATCCA 3036
                                                                         3028

Sau3AI                      Sau3AI
        BamHI     HinfI             BclI
          |        |                  |
3037 ATGGGATCCAACAAAGACTCAACAAATCTGGTTTGATCAGATACTTCAAACTATTTTGTATTCATTAAA 3105
      3041       3053              3069
      3041                         3069

HinfI
                                       |
3106 TTATGCAAGTGTCTCTTTATTGGTGAAGACTCTTTAGAAGCAAGAACGACAAGCAGTAATAAAAAAA 3174
                                        3135

3175 ACAAAGTTCAGTTTAAGATTTGTTATTGACTTATTGTCATTTGAAAAAATATAGTATGATTAATATA 3243
3244 GTTTTATTATATGCTTGTCTGTCTATTCAAGATTTGAGAACATTAATATGATACTGTCCACATATCCAA 3312
                         NdeI
                           |
3313 TATATTAAGTTTCATTTCTGTTCAAACATATGATAAGATGGTCAAATGATTATGAGTTTTGTTATTTAC 3381
                                          3341
              AluI TaqI         RsaI    Sau3AI
                |   |             |       |
3382 CTGAAGAAAAGATAAGTGAGCTTCGAGTTTCTGAAGGGTACGTGATCTTCATTTCTTGGCTAAAAGCGA 3450
                3402 3405                3421
                                          3425

3451 ATATGACATCACCTAGAGAAAGCCGATAATAGTAAACTCTGTTCTTGGTTTTTGGTTTAATCAAACCGA 3519
```

FIG. 2H

```
                              Mspl
                              Hpal
         Mspl     Ddel        |        Hinfl
         Hpal    Alul         Ndel     |
         |       |            |        |
3520 ACCGGTAGCTGAGTGTCAAGTCAGCAAACATGCAAACCATATGTCAATTCGTTAGATTCCCGGTTAA 3588
     |   |                              |                  |
     3522 3528                         3560               3576  3581
          3529                                                  3581
     Mspl
     Hpal
     |
3589 GTTGTAAACCGGTATTTCATTTGGTGAAAACCCTAGAAGCCAGCCANCCTTTTAATCTAATTTTGCA 3657
     |
     3598
     3598

Hinfl
                                                    HincII
                                 Ddel               BstNI
                                 |                  |         3718
3658 AACGAGAAGTCACCACCACCTCTCCACTAAAACCCTGAACCTTACTGAGAGAAGCAGAGNCANNAAAGAA 3726
                          |                              3715
                          3702                           3714

3727 CAAATAAAACCCGAAGATGAGACCACCACGTGCGGGGACGTTCAGGGGACGGGGAGGAAGAGAATGR 3795
      Avall                                                        Avall
      Alul                                                         |
      |                                                            |
3796 CGGCGG5MNTTTGGTGGCGGCGGACGTTTTGGTGGCGGCGGTGGACGTTTTGGTGGCGGCGGTGGA 3864
     |                                                              3863
     3801
        3804
          EcoRV  Avall                                          Ddel
          |     |                                               |
3865 CCTTTGGTGGTGGATATCGTGACGAAGGACCTCCCAGTGAAGTCATTGGTTCGTTACTCTTTTCTTAG 3933
                |      |                                    |
                3880   3892                                 3930
```

FIG. 21

```
                                    HindIII
                         Taq I       AluI                                    DdeI
                         HinfI        |                                        |
3934 TCGAATCTTATTCTGCTCTGCTCGTTGTTTACCGATAAAGCTTAAGACTTTATTGATAAAGTTCTCA 4002
         3937                       3974                               4000
         3935                       3976

AluI        XmnI                        HinfI   DdeI
      |           |                            |      |
4003 GCTTTGAATGTGAATGAACTGTTCCCTGCTTATTAGTGTCCTTTGTTTGAGTTGAATCACTGTCTTA 4071
     4004       4023                                4059      4069
          HinfI
               4085
         HincII
4072 GCACTTTGTTGTAGATTCATCTTTGTGTTAAGTAAAGGTAGAAACTTTGTGACTGTCTCCGTTATG 4140
     4146

AvaII AluI DdeI       Sau3AI
        |   |   |             |
4141 ACAAGGTTAACTTTGTTGGTTATAACAGAAGTTGCGACCTTTCTCCATGCTGTGTGAGGGTGATGCTGTG 4209

4210 GACCAAGCTCTCTCAGGCGAAGATCCCTTACTTCAATGCCCAATCTACTTGGAAAACAGACACAGAT 4278
     4210  4217 4222          4231

HindIII
            Sau3AI   AluI                      TaqI
              |       |                        SalI
                                          PstI HincII
                                            |  AccI  EcoRI
4279 TGGGAAAGTTGATGAGAGATCCAAGCTTGGGCTGCAGGTCGACGAATTC 4325
              4294  4302                  4313 4315  4321
                    4300                   4314 4316
```

FIG. 2J

Brassica campestris ACP Genomic Sequence

```
                  AccI
                  ┌──┐                                    DdeI
                                                       AluI AluI
                                                       ┌──┐ ┌──┐
  1 AAGAGTATGTCTACTACTACTCTATAATCAAGTTTCAAGAAGCTTGGCTCTCACTTTATAT    69
               11                                      46  51
                                                          47

70 GTTTGATGTTGTGTGCAGGTATGGTAAATCATGAAAGATAAAGAATGCAAACCCTGAAGTATTGG   138

DdeI
        ┌──┐
139 CAGAGAGGACTGAGGTGAGAGAGCATGTCACTTTGTGTTACTCATCTGAATTATCTTATATGCGAATT   207
        149

RsaI
    ┌──┐
208 GTAAGTGGTACTAAAAGGTTTGTAACTTTTGGTAGGTGGATTTGAAGGATAAATGGAGGAACTTGCTTC   276
    217
                                         HindIII         PvuII
                                         AluI           AluI
                                         ┌──┐           ┌──┐
277 GGTAGCGGGTAACAAGTTTTATATTGCTATGAAGCTTTTTTGCCTGCGTGACGTATCAGCAGCTGTGGAG   345
                                         310             338
                                         308             338
```

FIG. 3A

```
                                                       HindIII
                                                       AluI              AluI  AvaI
                                                        |                  |  |
967 AAGGCCCATGTTATCATAAAACGCCGTCGTTTGAGTGCACCAAGCTTATAAATGTAGCCAGCTACCTC 1035
     |                                                 1012             1029 1034
    HaeIII                                             1010
    971
                      RsaI                                    XhoI
                        |                                     TaqI  Sau3AI
                                                              AvaI  BglII    AvaI      TaqI
                                                               ||     |       |         |
1036 GGGACATCACGCTCTCTTTGTACACTCCGCCATCTCTCTCTCTCGAGCAGATCTCTCTCGGGAATATCG 1104
                      1055                                    1078 1085     1093      1103
                                                              1079 1085
                                                              1078

Tth111I
   TaqI
   SalI
   HincII
   AccI
   ||||
1105 ACAATGTCGACCACTTCTCGCTCTTCCGTCTCCATGCAAGCCACTTCTCTGGTAATCTCATCTCCTTCT 1173
   1112          METSerThrThrPheCysSerSerValSerMETGlnAlaThrSerLeu
   1110
   1111
   1112
   1108

Sau3AI
                         BclI                          Sau3AI              Sau3AI
                           |                             |                   |
1174 TGTGTTCCCAGATCGCTCTGATCATACTTTCTTTTAGATCATTGCCTCTGATCTGTTGCTTGATGTTT 1242
     |                      1193                        1210               1224
    Sau3AI                  1193
    1184
```

FIG. 3D

```
                                      AluI    HinfI
                                        |      |
1243 GTTAACTCTCCCACGCATGTTTGATTATGTTGAGAATTAGAAAAAAAATGTTAGCTTTACGAATCTTTAG 1311
                                              1296  1303

Sau3AI                                   TaqI
       |                                      Sau3AI
     BclI                                      ||
       |
1312 TGATCATTTCAATTGGATTTGCAATCTTGTGTGACATTTGAGGCTTGTGTAGATTTCGATCTGTATTCA 1380
     1313                                                        1369
     1313                                                      1368

HinfI  AluI                      DraI
                |     |                         |
1381 TTTTGAATCACAGCTATAATAGTCATTTGAGTAGTAGTGTTTTTAAATGAACATGTTTGTTGTATTGA 1449
     1386    1394                              1425

AluI
                                                     |
1450 TGGAACAAACAGGCAGCAACAACGAGGATTAGTTTCCAGAAGCCAGCTTTGGTTTCAACGACTAATCTC 1518
     AlaAlaThrThrArgIleSerPheGlnLysProAlaLeuValSerThrThrAsnLeu
                                            1496

HhaI                DdeI
                                            |                  |
1519 TCCTTCAACCTCCGCCGTTCAATCCCCACTCGTTCTCAATCTCCTGCGCGGTATGTTCTCATTCTCAG 1587
     SerPheAsnLeuArgArgSerIleProThrArgPheSerIleSerCysAla
                                           1568          1584
```

FIG. 3E

```
         TaqI          RsaI                                              HaeIII
         AluI
         |   |         |                                                 |
1588 CATTTATTCGAGCTTGCTTGTCATGGTACTCTCTCTAATTGTCTATTTGTTTATTAGGCCAAACCAG 1656
         1597                                                            AlaLysProG
              1601     1616                                              1648
                          DdeI                AluI
                          |                   |
1657 AGACGGTTGAGAAAGTGTCTAAGATAGTTAAGAAGCAGCTATCACTCAAAGACGACCAAAAGGTCGTTG 1725
     luThrValGluLysValSerLysIleValLysLysGlnLeuLysSerLeuLysAspAspGlnLysValValA
                               1676                                   1695

Sau3AI       HinfI  TaqI
                 |            |      |
1726 CGGGAGACCAAGTTTGCTGATCTTGAGCAGATTCTCTGACACTGTAAGTCATCAATCATTCTCTTATG 1794
     laGluThrLysPheAlaAspLeuGluGlnIleLeuAspThr
                          1743           1756  1763

DdeI           SphI
                                                          |              |
1795 TGAATAAAGAGAACTTGAAGAGTTTGTTTTTAACATATTAACTGAGTGTTTTGCATGCAGGTTGAGATA 1863
                                                          1837           ValGluIle
                                                                         1852

TaqI   DdeI
                                                        EcoRV  AluI
                                                        |      ||
1864 GTGATGGGTTTAGAGGAAGAGTTTGATATCGAAATGGCTGAAGAGAAAGCTCAGAAGATTGCTACTGTG 1932
     ValMetGlyLeuGluGluGluPheAspIleGluMetAlaGluGluLysAlaGlnLysIleAlaThrVal
                                       1891   1913
                                       1893   1914
```

FIG. 3F

```
                    AluI
                     SacI
                     AluI
1933 GAGGAAGCTGCTGAACTCATTGAAGAGCTCGTTCAACTTAAGAAGTAATTTTAGTATTAAGAGAGCAGCCA 2001
     GluGluAlaAlaGluLeuIleGluLeuIleGluGluValGlnLeuLysLys
                     1960
                        1962

HinfI
2002 AGGCTTTGTGTGGGTTTGTGTTTTCATAATCTTCCTGTCATTTCTTTTTCTTTAATGTGTCAAGCGAC 2069
                                                                        2070

TaqI
                                         SalI
                                         HincII
                       NcoI  Sau3AI       AccI
                        ——    ——          |||
2071 TCTGTGTTGGTTTAAAGTAGTATCTCGTTGCCATGGATCTCTCTCTATTGTCGACTGAAAACTTTTGGTT 2139
          DraI                         2100                2119
           ——                             2104             2120
          2082                                             2121

HindIII
      AluI
        ——
2140 TACACATGAAAGCTT 2154
           2150
           2152

FIG. 3G
```

Brassica Campestris Seed Specific cDNA-EA9

```
                        Sau3AI
                        ─┬─
 1  TTCAACTTTTCTAAACCAAATGGCTTTAACACAGATCCAAATCTTTCTCATTGTCTCTCTAGTCTCATC          69
                        METAlaLeuThrGlnIleGlnIleIlePheLeuIleValSerLeuValSerSe
                                                34

TaqI
    Sau3AI                                                       TaqI
    ClaI                                                         ─┬─
    ─┬─
    ─┬─
70  ATTCAGTTTATCGATCACTCTTTCTCGTCCATTACTCGATGAAGTCGCCATGCAAAGAGACATGCCGA          138
    rPheSerLeuSerIleThrLeuSerSerArgProLeuLeuAspLeuValAlaMETGlnLysArgHisAlaGl
    81                                          106
      82
      81

HaeIII
                                ─┬─
139 GTGGATGACCGAACACGGCCCGTGTTTACGCAGATGCGAACGAGAAAAACAACCGCTACGCTGTTTTCAA         207
    uTrpMETThrGluHisGlyMETThrGluValTyrArgValAlaAspAlaAsnGluLysAsnAsnArgTyrAlaValPheLy
                                                                157

HpaII                DraI
                                                ─┬─                  ─┬─
208 ACGCAACGTGGAACGCATTGAACGTTCAATCCGGACTAACGTTTAAACTCGGGTGAA                     276
    sArgAsnValGluArgIleGluArgLeuAsnAspValGlnSerGlyLeuThrPheLysLeuAlaValAlaAs
                                    250                         263
```

Complete nucleotide sequence of B. campestris cDNA EA9. The longest open reading frame is designated by three letter amino acid code. PolyA tails are evident at the end of the sequence and a potential polyadenylation signal is underlined.

FIG. 4A

```
       TaqI
       SalI
       HincII
       AluI AccI
       |||  |
553 AGAGCTTGTCGACTGCGACACAAACGATGGTGGCTGCATGGGCGGTTTGATGGATACAGCGTTTAACTA
    nGluLeuValAspCysAspThrAsnAspGlyGlyCysMETGlyGlyLeuMETAspThrAlaPheAsnTy
         557   562
         560
           561
             562                                                       621

622 CACAATAACTATTGGCGGCTTAACCTCTGAATCAAATTATCCTTATAAAGCACAAACGGCACTTGCAA
    rThrIleThrIleGlyGlyLeuThrSerGluSerAsnTyrProTyrLysSerThrArgGlyThrCysAs
                                                              HpaII
                                                              |
                                                                       690

691 CTTCAATAAAACTAAACAGATAGCAACTTCTATCAAAGGTTTTGAGGATGTCCCGGCTAACGATGAGAA
    nPheAsnLysThrLysGlnIleAlaThrSerIleLysGlyPheGluAspValProAlaAsnAspGluLy
                                                        744            759

760 AGCCCTAATGAAGGCAGTGGCACACACCCGGTTAGCATTGGAATAGCGGGAGGAGATATTGGTTTCCA
    sAlaLeuMETLysAlaValAlaHisProValSerIleGlyIleAlaGlyGlyAspIleGlyPheGl
                        HpaII                         Sau3AI
                        |                             BclI
                        789                           |                828

829 ATTCTATTCGTCGGTGTGTTCAGCGGGAGAATGCACAACTCATCTTGATCACGGGTAACTGCGGTTGG
    nPheTyrSerSerGlyValPheSerGlyValCysThrThrHisLeuAspHisGlyValThrAlaValGl
       HpaII
       |
       841                                            875
                                                        875            897
```

FIG. 4C

```
898 ATACGGCCGATCTAAAAACGGATTAAAGTACTGGATCCTCAAGAATTCATGGGGACCAAAATGGGAGA 966
    yTyrGlyArgSerLysAsnGlyLeuLysTyrTrpIleLeuLysAsnSerTrpGlyProLysTrpGlyGl
        904                       927        931     941          951
        906                       927        931

967 ACGTGGATACATGAGGATCAAAAAAGATATCAAGCCTAAACACGGACAATGTGCTCTTGCCATGAATGC 1035
    uArgGlyTyrMETArgIleLysLysAspIleLysLysProLysHisGlyGlnCysGlyLeuAlaMETAsnAl
                          982                995

1036 TTCGTACCCAACTATGTGAAAAAATCGGTTCAATATCCGGTTAAGCTTTAGAATAAATGTGTGTTGG 1104
     aSerTyrProThrMET                       1073  1081
         1041                                    1079

1105 TTATAATTTAAGACTCTGTTGCATGTAATTTGTGAAATGGTAAGTTTATGTGATGCAAAAGATTTGATA 1173

1174 AAAAAAAAAAAA 1186
```

FIG. 4D

SEED-SPECIFIC TRANSCRIPTIONAL REGULATION

CROSS-REFERENCE TO RELATED APPLICATIONS

This application is a continuation of application Ser. No.07/550,804, filed Jul. 9, 1990, now abandoned, which is a continuation-in-part of application Ser. No. 07/147,781, filed Jan. 25, 1988, now abandoned, which is a continuation-in-part of application Ser. No. 07/078,538, filed Jul. 28, 1987, now abandoned, which is a continuation-in-part of application Ser. No. 07/891,529, filed Jul. 31 1986, now abandoned.

INTRODUCTION

1. Technical Field

Genetic modification of plant material is provided for seed-specific transcription. Production of endogenous products may be modulated or new capabilities provided.

2. Background

In general, genetic engineering techniques have been directed to modifying the phenotype of individual prokaryotic and eukaryotic cells, especially in culture. Plant cells have-proven more intransigent than other eukaryotic cells due not only to the lack of suitable vector systems but also as a result of the different goals involved. Plant genetic engineering has for the most part been directed to modifying the entire plant or a particular tissue rather than modifying a single cell in culture.

For many applications, it will be desirable to provide for transcription in a particular plant tissue and/or at a particular time in the growth cycle of the plant or maturation cycle of the tissue. Toward this end, there is substantial interest in identifying endogenous plant products whose transcription or expression is regulated in a manner of interest. In identifying such products, one must first look for a product which appears at a particular time in the cell growth cycle or in a particular plant tissue, demonstrate its absence at other times or in other tissue, identify nucleic acid sequences associated with the product and then identify the sequence in the genome of the plant in order to obtain the 5'-untranslated sequence associated with transcription. Identifying the particular sequence, followed by establishing that it is the correct sequence and isolating the desired transcriptional regulatory region requires an enormous outlay in time and effort. One must then prepare appropriate constructs, and demonstrate that the constructs are efficacious in the desired manner.

Identifying such sequences is a challenging project, subject to numerous pitfalls and uncertainty. There is, however, substantial interest in being able to genetically modify plants, which justifies the substantial expenditures and efforts in identifying transcriptional regulatory sequences and manipulating them to determine their utility.

Relevant Literature

Crouch et al., In: *Molecular Form and Function of the Plant Genome*, eds. van Vloten-Doting, Groot and Hall, Plenum Publishing Corp. 1985, pp 555–566; Crouch and Sussex, *Planta* (1981) 153:64–74; Crouch et al., *J. Mol. Appl. Genet.* (1983) 2:273–283; Simon et al., *Plant Molecular Biology* (1985) 5:191–201; and Scofield and Crouch, *J. Biol. Chem.* (1987) 262:12202–12208, describe various aspects of *Brassica napus* storage proteins. Rose et al., *Nucl. Acids Res.* (1987) 15:7197 and Scherer and Knauf, *Plant Mol. Biolo* (1987) 9:127–134 describe ACP genes. Beachy et al., *EMBO J.* (1985) 4:3047–3053; Sengupta-Gopalan et al., *Proc. Natl. Acad. Sci. USA* (1985) 82:3320–3324; Greenwood and Chrispeels, *Plant Physiol.* (1985) 79:65–71 and Chen et al., *Proc. Natl. Acad. Sci. USA* (1986) 83:8560–8564 describe studies concerned with seed storage proteins and genetic manipulation. Eckes et al., *Mol. Gen. Genet.* (1986) 205:14–22 and Fluhr et al., *Science* (1986) 232:1106–1112 describe the genetic manipulation of light inducible plant genes.

SUMMARY OF THE INVENTION

DNA constructs are provided which are employed in manipulating plant cells to provide for seed-specific transcription. Particularly, transcriptional regions from seed storage proteins, seed coat proteins or acyl carrier protein are joined to other than the homologous gene and introduced into a plant cell host for integration into the genome to provide for seedspecific transcription. The constructs provide for modulation of expression of endogenous products as well as production of exogenous products in the seed.

DESCRIPTION OF THE DRAWINGS

FIG. 2 is a restriction map of cloned λCGN1-2 showing the entire coding region sequence as well as extensive 5' upstream and 3' downstream sequences.

DESCRIPTION OF THE SPECIFIC EMBODIMENTS

Figure 1B:
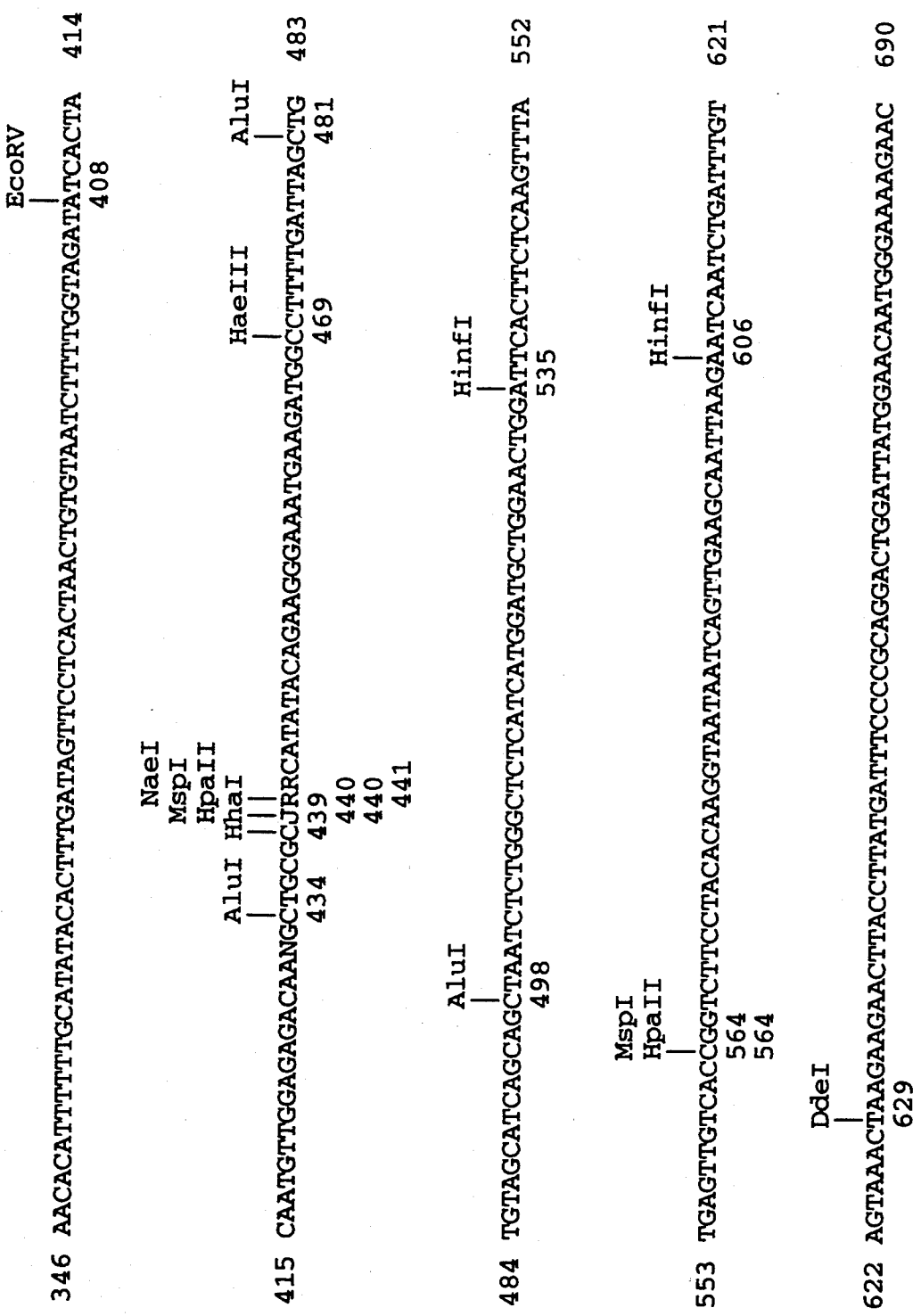
FIG. 1 is a partial sequence of the promoter region of the λBnNa napin gene. The start (ATG) of the open reading frame is underlined.

In accordance with the subject invention, novel DNA constructs are provided which allow for modification of transcription in seed, particularly in embryos during seed maturation. The DNA constructs comprise a regulated transcriptional initiation region associated with seed formation, preferably in association with embryogenesis and seed maturation.

Downstream from and under the transcriptional initiation regulation of the seed-specific region will be a sequence of interest which will provide for modification of the phenotype of the seed, by modulating the production of an endogenous product, as to amount, relative distribution, or the like, or production of an exogenous expression product to provide for a novel function or product in the seed. The DNA construct will also provide for a termination region, so as to provide an expression cassette into which a gene may be introduced. Conveniently, transcriptional initiation and termination regions may be provided separated in the direction of transcription by a linker or polylinker having one or a plurality of restriction sites for insertion of the gene to be under the transcriptional regulation of the regulatory regions. Usually, the linker will have from 1 to 10, more usually from about 1 to 8, preferably from about 2 to 6 restriction sites. Generally, the linker will be fewer than 100 bp, frequently fewer than 60 bp and generally at least about 5 bp.

The transcriptional initiation region may be native or homologous to the host or foreign or heterologous to the host. By foreign is intended that the transcriptional initiation region is not found in the wild-type host into which the transcriptional initiation region is introduced.

Of particular interest are those transcriptional initiation regions associated with storage proteins, such as napin, cruciferin, β-conglycinin, phaseolin, or the like, and proteins involved in fatty acid biosynthesis, such as acyl carrier protein (ACP). The transcriptional initiation regions may be obtained from any convenient host, particularly plant hosts such as Brassica, e.g napus or campestris, soybean (*Glycine max*), bean (*Phaseolus vularis*), corn (*Zea mays*), cotton (Gossypium sp.), safflower (*Carthamus tinctorius*), tomato (*Lycopersicon esculentum*), and Cuphea species. Other transcriptional initiation regions of particular interest are those associated with seed embryo genes that are expressed in the period from about day 7 to day 40, particularly those having maximum expression in the period from about day 10 to about day 30, postanthesis, and seed coat genes which are expressed in the period from about day 11 to day 30. Usually the period of expression will be at least 3 days, more usually about 7 days and may be substantially over the entire period.

A transcriptional initiation region may be used for varying the phenotype of the seeds. Various changes in phenotype are of interest. These include modifying the fatty acid composition in seeds, that is changing the ratio and/or amounts of the various fatty acids, as to length, unsaturation, or the like. Thus, the fatty acid composition may be varied by enhancing the fatty acids of from 10 to 14 carbon atoms as compared to the fatty acids of from 16 to 18 carbon atoms, increasing or decreasing fatty acids of from 20 to 24 carbon atoms, providing for an enhanced proportion of fatty acids which are saturated or unsaturated, or the like. These results can be achieved by providing for reduction of expression of one or more endogenous products, particularly enzymes or cofactors, by producing a transcription product which is complementary to the transcription product of a native gene, so as to inhibit the maturation and/or expression of the transcription product, or providing for expression of a gene, either endogenous or exogenous, associated with fatty acid synthesis. Expression products associated with fatty acid synthesis include acyl carrier protein, acyl-ACP thioesterase, acetyl-CoA ACP transacylase, acetyl-CoA carboxylase, ketoacyl-ACP synthases, malonyl-CoA ACP transacylase, stearoyl-ACP desaturase, and other desaturase enzymes.

Alternatively, one may provide various products from other sources including mammals, such as blood factors, lymphokines, colony stimulating factors, interferons, plasminogen activators, enzymes, e.g. superoxide dismutase, chymosin, etc., hormones, rat mammary thioesterase 2, phospholipid acyl desaturases involved in the synthesis of eicosapentaenoic acid, human serum albumin. The level of seed proteins, particularly mutated seed proteins, having an improved amino acid distribution which would be better suited to the nutrient value of the seed can also be increased. This can be achieved, for example, by inhibition of the native seed protein by producing a complementary DNA sequence to the native coding region or non-coding region, where the complementary sequence does not hybridize efficiently to the mutated sequence, or inactivates the native transcriptional capability.

The transcriptional cassette will include in the 5'-3' direction of transcription, a transcriptional and translational initiation region, a DNA sequence of interest, and a transcriptional and translational termination region functional in plants. One or more introns may also be present. The DNA sequence may have any open reading frame encoding a peptide of interest, e.g. an enzyme, or a sequence complementary to a genomic sequence, where the genomic sequence may be an open reading frame, an intron, a non-coding leader sequence, or any other sequence where the complementary sequence will inhibit transcription, messenger RNA processing, e.g. splicing, or translation. The DNA sequence of interest may be synthetic, naturally derived, or combinations thereof. Depending upon the nature of the DNA sequence of interest, it may be desirable to synthesize the sequence with plant preferred codons. The plant preferred codons may be determined from the codons of highest frequency in the proteins expressed in the largest amount in the particular plant species of interest.

In preparing the transcription cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, or the like may be employed, where insertions, deletions or substitutions, e.g. transitions and transversions, may be involved.

The termination region which is employed will be primarily one of convenience, since the termination regions appear to be relatively interchangeable. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions.

By appropriate manipulations, such as restriction, chewing back or filling in overhangs to provide blunt ends, ligation of linkers, or the like, complementary ends of the fragments can be provided for joining and ligation.

In carrying out the various steps, cloning is employed, so as to amplify the amount of DNA and to allow for analyzing the DNA to ensure that the operations have occurred in a proper manner. A wide variety of cloning vectors are available, where the cloning vector includes a replication system functional in *E. coli* and a marker which allows for selection of the transformed cells. Illustrative vectors include pBR332, the pUC series, the M13 mp series, pACYC184, etc. Thus, the sequence may be inserted into the vector at an appropriate restriction site(s), the resulting plasmid used to transform the *E. coli* host, the *E. coli* grown in an appropriate nutrient medium and the cells harvested and lysed and the plasmid recovered. Analysis may involve sequence analysis, restriction analysis, electrophoresis, or the like. After each manipulation the DNA sequence to be used in the final construct may be restricted and joined to the next sequence, where each of the partial constructs may be cloned in the same or different plasmids.

Depending upon the manner of introduction of the transcription construct into the host plant, other DNA sequences may be required. For example, when using the Ti- or Ri-plasmid for transformation of plant cells, as described below, at least the right border and frequently both the right and left borders of the T-DNA of the Ti- and Ri-plasmids will be joined as flanking regions to the transcription construct. The use of T-DNA for transformation of plant cells has received extensive study and is amply described in EPA Serial No. 120,516, Hoekema, In: The Binary Plant Vector System Offset -drukkerij Kanters B. V., Alblasserdam, 1985, Chapter V, Fraley, et al., *Crit. Rev. Plant Sci.*, 4:1–46, and An et al., *EMBO J.* (1985) 4:277–284.

Alternatively to enhance integration into the plant genome, terminal repeats of transposons may be used as borders in conjunction with a transposase. In this situation, expression of the transposase should be inducible, or the transposase inactivated, so that once the transcription construct is integrated into the genome, it should be relatively stably integrated to avoid hopping.

The transcription construct will normally be joined to a marker for selection in plant cells. Conveniently, the marker may be resistance to a biocide, particularly an antibiotic, such as kanamycin, G418, bleomycin, hygromycin, chloramphenicol, or the like. The particular marker employed will be one which will allow for selection of transformed cells as compared to cells lacking the DNA which has been introduced.

A variety of techniques are available for the introduction of DNA into a plant cell host. These techniques include transformation with Ti-DNA employing *A. tumefaciens* or *A. rhizogenes* as the transforming agent, protoplast fusion, injection, electropotation, etc. For transformation with Arobacterium, plasmids can be prepared in *E. coli* which plasmids contain DNA homologous with the Ti-plasmid, particularly T-DNA. The plasmid may or may not be capable of replication in Arobacterium, that is, it may or may not have a broad spectrum prokaryotic replication system, e.g. RK290, depending in part upon whether the transcription construct is to be integrated into the Ti-plasmid or be retained on an independent plasmid. By means of a helper plasmid, the transcription construct may be transferred to the *A. tumefaciens* and the resulting transformed organism used for transforming plant cells.

Conveniently, explants may be cultivated with *A. tumefaciens* or *A. rhizogenes* to allow for transfer of the expression cassette to the plant cells, the plant cells dispersed in an appropriate selective medium for selection, grown to callus, shoots grown and plantlets regenerated from the shoots by growing in rooting medium. The Arobacterium host will contain a plasmid having the vir genes necessary for transfer of the T-DNA to the plant cells and may or may not have T-DNA. For injection and electroporation, disarmed Ti-plasmids (lacking the tumor genes, particularly the T-DNA region) may be used to introduce genes into the plant cell.

The cells which have been transformed may be grown into plants in accordance with conventional ways. See, for example, McCormick et al., *Plant Cell Reports* (1986) 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

As a host cell, any plant variety may be employed which provides a seed of interest. Thus, for the most part, plants will be chosen where the seed is produced in high amounts or a seed-specific product of interest is involved. Seeds of interest include the oil seeds, such as the Brassica seeds, cotton seeds, soybean, safflower, sunflower, or the like; grain seeds, e.g. wheat, barley, rice, clover, corn, or the like.

Identifying useful transcriptional initiation regions may be achieved in a number of ways. Where a seed protein has been or is isolated, it may be partially sequenced, so that a probe may be designed for identifying messenger RNA specific for seed. To further enhance the concentration of the messenger RNA specifically associated with seed, cDNA may be prepared and the cDNA subtracted with messenger RNA or cDNA from non-seed associated cells. The residual cDNA may then be used for probing the genome for complementary sequences, using an appropriate library prepared from plant cells. Sequences which hybridize to the cDNA may then be isolated, manipulated, and the 5'-untranslated region associated with the coding region isolated and used in expression constructs to identify the transcriptional activity of the 5'-untranslated region.

In some instances, a probe may be employed directly for screening a genomic library and identifying sequences which hybridize to the probe. The sequences will be manipulated as described above to identify the 5'-untranslated region.

The expression constructs which are prepared employing the 5'-untranslated regions may be transformed into plant cells as described previously for evaluation of their ability to function with a heterologous structural gene (i.e., a gene other than the open reading frame associated with the 5'-untranslated region) and the seed-specificity. In this manner, specific sequences may be identified for use with sequences for seed-specific transcription. Of particular interest are transcriptional initiation regions from napin genes, particularly Brassica napin genes, more particularly *Brassica napus* or *Brassica campestris* genes; transcriptional initiation regions regulating structural genes associated with lipid production, particularly fatty acid production, including acyl carrier proteins, which may be endogenous or exogenous to the particular plant, such as spinach acyl carrier protein, Brassica acyl carrier protein (either napus or campestris), uphea acyl carrier protein, acetyl-CoA ACP transacylase, malonyl-CoA ACP transacylase, β-ketoacyl-ACP synthases I and II, acyl-ACP thioesterase, particularly thioesterase II, from plant, mammalian, or bacterial sources, for example rat thioesterase II, acyl ACP, or phospholipid acyl desaturases.

The following examples are offered by way of illustration and not by way of limitation.

EXPERIMENTAL

Materials and Methods

Clonin Vectors

Cloning vectors used include the pUC vectors, pUC8 and pUC9 (Vieira and Messing, *Gene* (1982) 19:259–268); pUC18 and pUC19 (Norrander et al., *Gene* (1983) 26:101–106; Yanisch-Perron et al., *Gene* (1985) 33:103–119), and analogous vectors exchanging chloramphenicol resistance (CAM) as a marker for the ampicillin resistance of the pUC plasmids described above (pUC-CAM [pUC12-Cm, pUC13-Cm] Buckley, K., Ph.D. Thesis, U.C.S.D., CA 1985). The multiple cloning sites of pUC18 and pUC19 vectors were exchanged with those of pUC-CAM to create pCGN565 and pCGN566 which are CAM resistant. Also used were pUC118 and pUC119, which are respectively, pUC18 and pUC19 with the intergenic region of M13, from an HgiAI site at 5465 to the AhaIII site at 5941, inserted at the NdeI site of pUC (available from Vieira J. and Messing, J. Waksman Institute, Rutgers University, Rutgers, N.J.)

Materials

Terminal deoxynucleotide transferase (TDT), RNaseH, *E. coli* DNA polymerase, T4 kinase, and restriction enzymes were obtained from Bethesda Research Laboratories; *E. coli* DNA ligase was obtained from New England Biolabs; reverse transcriptase was obtained from Life Sciences, Inc.; isotopes were obtained from Amersham; X-gal was obtained from Bachem, Inc. Torrance, Calif.

Example I

Construction of a Napin Promoter

There are 298 nucleotides upstream of the ATG start codon of the napin gene on the pgN1 clone, a 3.3 kb EcoRI fragment of *B. napus* genomic DNA containing a napin gene cloned into pUC8 (available from Marti Crouch, University of Indiana). pgN1 DNA was digested with EcoRI and SstI and ligated to EcoRI/SstI digested pCGN706. (pCGN706 is an XhoI/PstI fragment containing 3' and polyadenylation sequences of another napin cDNA clone pN2 (Crouch et al., 1983 supra) cloned in pCGN566 at the SalI and PstI sites.) The resulting clone pCGN707 was digested with SalI and treated with the enzyme Bal31 to remove some of the coding region of the napin gene. The resulting resected DNA was digested with SmaI after the Bal31 treatment and religated. One of the clones, pCGN713, selected by size, was subcloned by EcoRI and BamHI digestion into both Eco. RI-BamHI digested pEMBL18 (Dente et al., *Nucleic Acids Res.* (1983) 11:1645–1655) and pUC118 to give E418 and E4118 respectively. The extent of Bal31 digestion was confirmed by Sanger dideoxy sequencing of E418 template. The Bal31 deletion of the promoter region extended only to 57 nucleotides downstream of the start codon, thus containing the 5' end of the napin coding sequence and about 300 bp of the 5' non-coding region. E4118 was tailored to delete all of the coding region of napin including the ATG start codon by in vitro mutagenesis by the method of Zoller and Smith (*Nucleic Acids Res.* (1982) 10:6487–6500) using an oligonucleotide primer 5'-GATGTTTTGTATGTGGGCCCCTAGGAGATC-3'. Screening for the appropriate mutant was done by two transformations into *E. coli* strain JM83 (Messing J., In: Recombinant DNA Technical Bulletin, NIH Publication No. 79–99, 2 No. 2, 1979, pp 43–48) and SmaI digestion of putative transformants. The resulting napin promoter clone is pCGN778 and contains 298 nucleotides from the EcoRI site of pgN1 to the A nucleotide just before the ATG start codon of napin. The promoter region was subcloned into a chloramphenicol resistant background by digestion with EcoRI and BamHI and ligation to EcoRIBamHI digested pCGN565 to give pCGN779c.

Figure 1C:
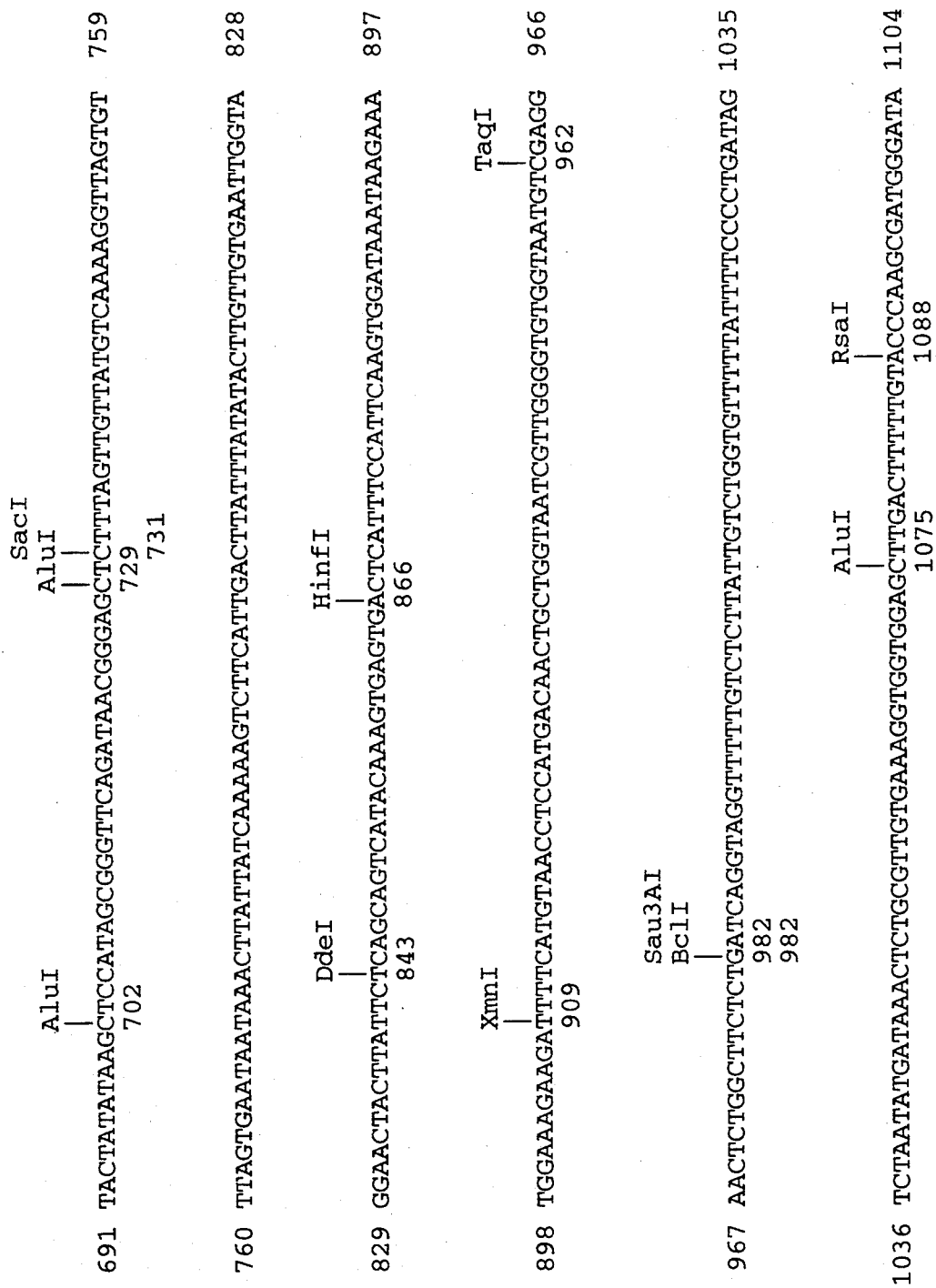
Figure 1F:
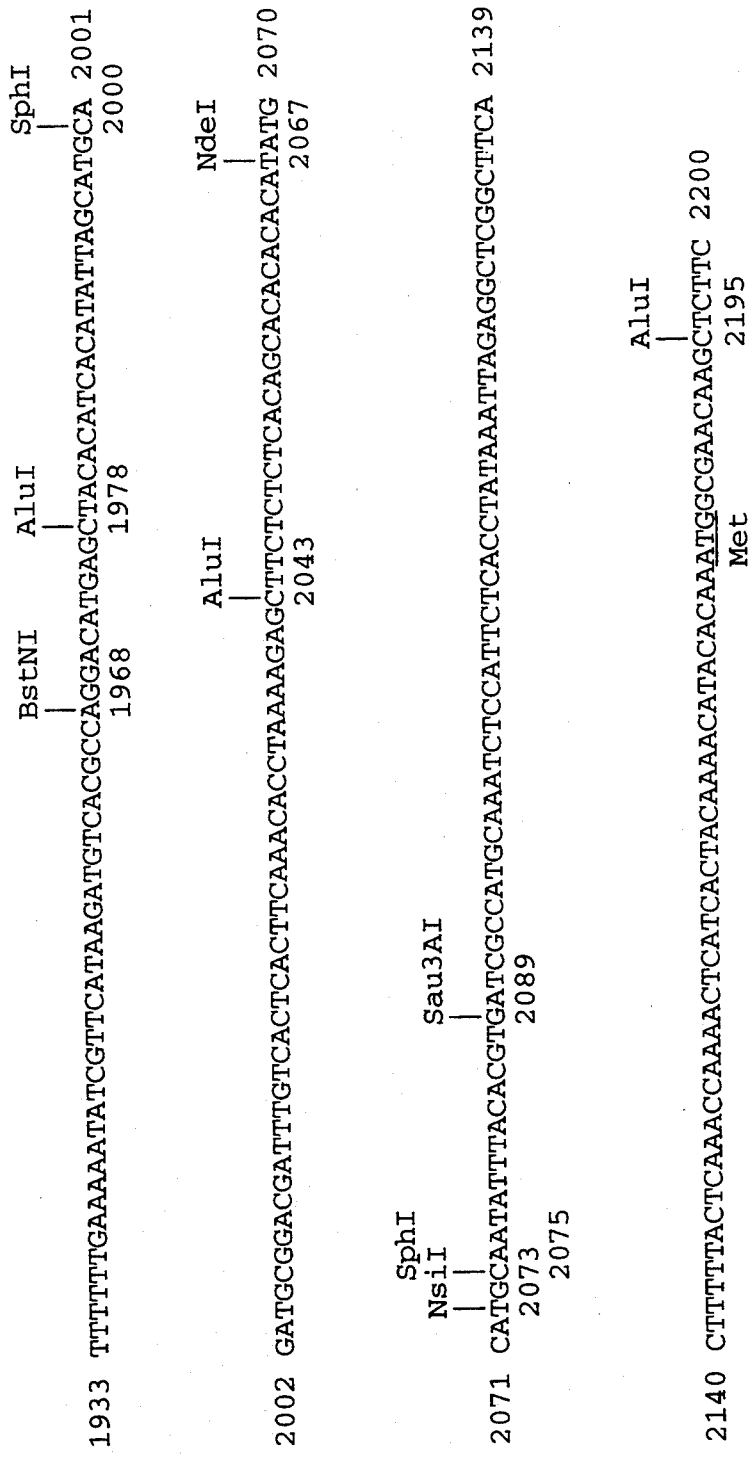

Extension of the Napin Promoter Clone pCGN779c contains only 298 nucleotides of potential 5'-regulatory sequence. The napin promoter was extended with a 1.8 kb fragment found upstream of the 5'-EcoRI site on the original λBnNa clone. The ~-3.5 kb XhoI fragment of λBnNa (available from M. Crouch), which includes the napin region, was subcloned into SalI-digested pUC119 to give pCGN930. A HindIII site close to a 5' XhoI site was used to subclone the HindIII-EcoRI fragment of pCGN930 into HindIII-EcoRI digested Bluescript+(Vector Cloning Systems, San Diego, Calif.) to give pCGN942. An extended napin promoter was made by ligating pCGN779c digested with EcoRI and PstI and pCGN942 digested with EcoRI and PstI to make pCGN943. This promoter contains ~2.1 kb of sequence upstream of the original ATG of the napin gene contained on λBnNa. A partial sequence of the promoter region is shown in FIG. 1.

Napin Cassettes

The extended napin promoter and a napin 3'-regulatory region are combined to make a napin cassette for expressing genes seed-specifically. The napin 3'-region used is from the plasmid pCGN1924 containing the XhoI-EcoRI fragment from pgN1 (XhoI site is located 18 nucleotides from the stop codon of the napin gene) subcloned into EcoRI-SalI digested pCGN565. HindIII-PstI digested pCGN943 and pCGN1924 are ligated to make the napin cassette pCGN944, with unique cloning sites SmaI, SalI, and PstI for inserting genes.

Construction of cDNA Library from Spinach Leaves

Total RNA was extracted from young spinach leaves in 4M guanidine thiocyanate buffer as described by Facciotti et al. (*Biotechnology* (1985) 3:241–246). Total RNA was subjected to oligo(dT)-cellulose column chromatography two times to yield poly(A)+ RNA as described by Maniatis et al., (1982) *Molecular Cloning: A Laboratory Manual*, Cold Spring Harbor Laboratory, N. Y. A cDNA library was constructed in pUC13-Cm according to the method of Gubler and Hoffman, (*Gene* (1983) 25:263–269) with slight modifications. RNasin was omitted in the synthesis of first strand cDNA as it interfered with second strand synthesis if not completely removed, and dCTP was used to tail the vector DNA and dGTP to tail double-stranded cDNA instead of the reverse as described in the paper. The annealed cDNA was transformed to competent *E. coli* JM83 (Messing (1979)supra) cells according to Hanahan (*J. Mol. Biol.* (1983) 166:557–580) and spread onto LB agar plates (Miller (1972) Experiments in Molecular Genetics. Cold Spring Harbor Laboratory, Cold Spring Harbor, N.Y.) containing 50 μg/ml chloramphenicol and 0.005% X-Gal.

Identification of Spinach ACP-I cDNA

A total of approximately 8000 cDNA clones were screened by performing Southern blots (Southern, *J. Mol. Biol.* (1975) 98:503) and dot blot (described below) hybridizations with clone analysis DNA from 40 pools representing 200 cDNA clones each (see below). A 5' end-labeled synthetic oligonucleotide (ACPP4) that is at least 66% homologous with a 16 amino acid region of spinach ACP-I (5'-GATGTCTTGAGCCTTGTCCT-CATCCACATTGATACCAAACTCCTCCTC-3') is the complement to a DNA sequence that could encode the 16 amino acid peptide glu-glu-glu-phe-gly-ile-asnval-asp-glu-asp-lys-ala-gln-asp-ile, residues 49-64 of spinach ACP-I (Kuo and Ohlrogge, *Arch. Biochem. Biophys.* (1984) 234:290-296) and was used for an ACP probe.

Clone analysis DNA for Southern and dot blot hybridizations was prepared as follows. Transformants were transferred from agar plates to LB containing 50 μg/ml chloramphenicol in groups of ten clones per 10 ml media. Cultures were incubated overnight in a 37° C. shaking incubator and then diluted with an equal volume of media and allowed to grow for 5 more hours. Pools of 200 cDNA clones each were obtained by mixing contents of 20 samples. DNA was extracted from these cells as described by Birnboim and Doly (*Nucleic Acids Res.* (1979) 7:1513-1523). DNA was purified to enable digestion with restriction enzymes by extractions with phenol and chloroform followed by ethanol precipitation. DNA was resuspended in sterile, distilled water and 1 μg of each of the 40 pooled DNA samples was digested with EcoRI and HindIII and electrophoresed through 0.7% agarose gels. DNA was transferred to nitrocellulose filters following the blot hybridization technique of Southern.

ACPP4 was 5' end-labeled using γ-$^{32}$P dATP and T4 kinase according to the manufacturer's specifications. Nitrocellulose filters from Southern blot transfer of clone analysis DNA were hybridized (24 hours, 42° C.) and washed according to Berent et al. (*BioTechniques* (1985) 3:208-220). Dot blots of the same set of DNA pools were prepared by applying 1 μg of each DNA pool to nylon membrane filters in 0.5M NaOH. These blots were hybridized with the probe for 24 hours at 42° C. in 50% formamide/1% SDS/1M NaCl, and washed at room temperature in 2X SSC/0.1% SDS (1X SSC×0.15M NaCl; 0.015M Na citrate; SDS-sodium dodecylsulfate). DNA from the pool which was hybridized by the ACPP4 oligoprobe was transformed to JM83 cells and plated as above to yield individual transformants. Dot blots of these individual cDNA clones were prepared by applying DNA to nitrocellulose filters which were hybridized with the ACPP4 oligonucleotide probe and analyzed using the same conditions as for the Southern blots of pooled DNA samples.

Nucleotide Sequence Analysis

The positive clone, pCGN1SOL, was analyzed by digestion with restriction enzymes and the following partial map was obtained.

pCGN1SOL contains an (approximately) 700 bp cDNA insert including a stretch of A residues at the 3' terminus which represents the poly(A) tail of the mRNA. An ATG codon at position 61 is presumed to encode the MET translation initiation codon. This codon is the start of a 411 nucleotide open reading frame, of which, nucleotides 229-471 encode a protein whose amino acid sequence corresponds almost perfectly with the published amino acid sequence of ACP-I of Kuo and Ohlrogge supra as described previously. In addition to mature protein, the pCGN1SOL also encodes a 56 residue transit peptide sequence, as might be expected for a nuclear-encoded chloroplast protein.

Napin—ACP Construct pCGN796 was constructed by ligating pCGN1SOL digested with HindIII-BamHI, pUC8-CM digested with HindIII and BamHI and pUC118 digested with BamHI. The ACP gene from pCGN796 was transferred into a chloramphenicol background by digestion with BamHI and ligation with BamHI digested pCGN565. The resulting pCGN1902 was digested with EcoRI and SmaI and ligated to EcoRI-SmaI digested pUC118 to give pCGN1920. The ACP gene in pCGN1920 was digested at the NcoI site, filled in by treatment with the Klenow fragment, digested with SmaI and religated to form pCGN1919. This eliminated the 5'-coding sequences from the ACP gene and regenerated the ATG. This ACP gene was flanked with PstI sites by digesting pCGN1919 with EcoRI, filling in the site with the Klenow fragment and ligating a PstI linker. This clone is called pCGN945.

The ACP gene of pCGN945 was moved as a BamHI-PstI fragment to pUC118 digested with BamHI and PstI to create pCGN945a so that a SmaI site (provided by the pUC118) would be at the 5'-end of the ACP sequences to facilitate cloning into the napin cassette pCGN944. pCGN945a digested with SmaI and PstI was ligated to pCGN944 digested with SmaI and PstI to produce the napin ACP cassette pCGN946. The napin ACP cassette was then transferred into the binary vector pCGN783 by cloning from the HindIII site to produce pCGN948.

Construction of the Binary Vector pCGN783 pCGN783 is a binary plasmid containing the left and right T-DNA borders of *A. tumefaciens* (Barker et al., *Plant Mol. Biol.* (1983) 2:335-350); the gentamicin resistance gene of pPH1JI (Hirsch et al., *Plasmid* (1984),

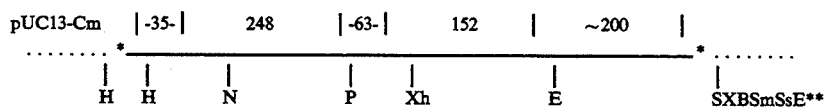

H—HindIII    N—NcoI    P—PvuII    Xh—XhoI
E—EcoRI      S—SalI    X—XbaI     Sm—SmaI
B—BamHI      Ss—SstI

*former PstI site destroyed with tailing
**polylinker with available restriction sites indicated The cDNA clone was subcloned into pUC118 and pUC119 using standard laboratory techniques of restriction, ligation, transformation, and analysis (Maniatis et al., (1982) supra). Single-stranded DNA template was prepared and DNA sequence was determined using the Sanger dideoxy technique (Sanger et al., *Proc. Nat. Acad. Sci. USA* (1977) 74:5463-5467). Sequence analysis was performed using a software package from Intelli-Genetics, Inc.

12:139-141) the 35S promoter of cauliflower mosaic virus (CaMV) (Gardner et al., *Nucleic Acids Res.* (1981) 9:2871-2890), the kanamycin resistance gene of Tn5 (Jorgenson et al., infra and Wolff et al., *Nucleic Acids Res.* (1985) 13:355-367) and the 3' region from transcript 7 of pTiA6 (Barker et al., (1983) supra).

To obtain the gentamicin resistance marker, the gentamicin resistance gene was isolated as a 3.1 kb EcoRI-PstI fragment of pPHIJ1 cloned into pUC9 yielding pCGN549. The HindIII-BamHI fragment containing the gentamicin resistance gene was substituted for the HindIII-BglII fragment of pCGN587 creating pCGN594.

pCGN587 was prepared as follows: The HindIII-SmaI fragment of Tn5 containing the entire structural gene for APHII (Jorgenson et al., *Mol. Gen. Genet.* (1979) 177:65) was cloned into pUC8 Vieira and Messing, Gene (1982) 19:259), converting the fragment into a HindIII-EcoRI fragment, since there is an EcoRI site immediately adjacent to the SmaI site. The PstI-EcoRI fragment containing the 3'-portion of the APHII gene was then combined with an EcoRI-BamHI-SalI-PstI linker into the EcoRI site of pUC7 (pCGN546W). Since this construct does not confer kanamycin resistance, kanamycin resistance was obtained by inserting the BglII-PstI fragment of the APHII gene into the BamHI-PstI site (pCGN546X). This procedure reassembles the APHII gene, so that EcoRI sites flank the gene. An ATG codon was upstream from and out of reading frame with the ATG initiation codon of APHII. The undesired ATG was avoided by inserting a Sau3A-PstI fragment from the 5'-end of APHII, which fragment lacks the superfluous ATG, into the BamHI-PstI site of pCGN546W to provide plasmid pCGN550.

The EcoRI fragment containing the APHII gene was then cloned into the unique EcoRI site of pCGN451, which contains an octopine synthase cassette for expression, to provide pCGN552 (1 ATG).

pCGN451 includes an octopine cassette which contains about 1556 bp of the 5' non-coding region fused via an EcoRI linker to the 3' non-coding region of the octopine synthase gene of pTiA6. The pTi co-ordinates are 11,207 to 12,823 for the 3' region and 13,643 to 15,208 for the 5' region as defined by Barker et al., *Plant Mol. Biol.* (1983) 2:325.

The 5' fragment was obtained as follows. A small subcloned fragment containing the 5' end of the coding region, as a BamHI-EcoRI fragment was cloned in pBR322 as plasmid pCGN407. The BamHI-EcoRI fragment has an XmnI site in the coding region, while pBR322 has two XmnI sites. pCGN407 was digested with XmnI, resected with Bal31 nuclease and EcoRI linkers added to the fragments. After EcoRI and BamHI digestion, the fragments were size fractionated, the fractions cloned and sequenced. In one case, the entire coding region and 10 bp of the 5' non-translated sequences had been removed leaving the 5' non-translated region, the mRNA cap site and 16 bp of the 5' non-translated region (to a BamHI site) intact. This small fragment was obtained by size fractionation on a 7% acrylamide gel and fragments approximately 130 bp long eluted.

This size fractionated DNA was ligated into M13mp9 and several clones sequenced and the sequence compared to the known sequence of the octopine synthase gene. The M13 construct was designated p14, which plasmid was digested with BamHI and EcoRI to provide the small fragment which was ligated to a XhoI to BamHI fragment containing upstream 5' sequences from pTiA6 (Garfinkel and Nester, *J. Bacteriol.* (1980) 144:732) and to an EcoRI to XhoI fragment containing the 3' sequences.

The resulting XhoI fragment was cloned into the XhoI site of a pUC8 derivative, designated pCGN426. This plasmid differs from pUC8 by having the sole EcoRI site filled in with DNA polymerase I, and having lost the PstI and HindIII site by nuclease contamination of HincII restriction endonuclease, when a XhoI linker was inserted into the unique HincII site of pUC8. The resulting plasmid pCGN451 has a single EcoRI site for the insertion of protein coding sequences between the 5' non-coding region (which contains 1,550 bp of 5' non-transcribed sequence including the right border of the T-DNA, the mRNA cap site and 16 bp of 5' non-translated sequence) and the 3' region (which contains 267 bp of the coding region, the stop codon, 196 bp of 3' non-translated DNA, the polyA site and 1,153 bp of 3' nontranscribed sequence). pCGN451 also provides the right T-DNA border.

The resulting plasmid pCGN451 having the ocs 5' and the ocs 3' in the proper orientation was digested with EcoRI and the EcoRI fragment from pCGN551 containing the intact kanamycin resistance gene inserted into the EcoRI site to provide pCGN552 having the kanamycin resistance gene in the proper orientation.

This ocs/KAN gene was used to provide a selectable marker for the trans type binary vector pCGN587.

The 5' portion of the engineered octopine synthase promoter cassette consists of pTiA6 DNA from the XhoI at bp 15208-13644 (Barker's numbering), which also contains the T-DNA boundary sequence (border) implicated in T-DNA transfer. In the plasmid pCGN587, the ocs/KAN gene from pCGN552 provides a selectable marker as well as the right border. The left boundary region was first cloned in M13mp9 as a HindIII-SmaI piece (pCGN502) (base pairs 602-2213) and recloned as a KpnI-EcoRI fragment in pCGN565 to provide pCGN580. pCGN565 is a cloning vector based on pUC8-Cm, but containing pUC18 linkers. pCGN580 was linearized with BamHI and used to replace the smaller BglII fragment of pVCK102(Knauf and Nester, Plasmid 1982) 8:45), creating pCGN585. By replacing the smaller SalI fragment of pCGN585 with the XhoI fragment from pCGN552 containing the ocs/-KAN gene, pCGN587 was obtained.

The pCGN594 HindIII-BamHI region, which contains an 5' -ocs-kanamycin-ocs-3'(ocs is octopine synthase with 5' designating the promoter region and 3' the terminator region, see U.S. application Ser. No. 775,923, filed Sep. 13, 1985) fragment was replaced with the HindIII-BamHI polylinker region from pUC18.

pCGN566 contains the EcoRI-HindIII linker of pUC18 inserted into the EcoRI-HindIII sites of pUC13-Cm. The HindIII-BglII fragment of pNW31C-8,29-1 (Thomashow et al., Cell (1980) 19:729) containing ORF1 and -2 of pTiA6 was subcloned into the HindIII-BamHI sites of pCGN566 producing pCGN703.

The Sau3A fragment of pCGN703 containing the 3' region of transcript 7 (corresponding to bases 2396-2920 of pTiA6 (Barker et al., (1983) supra) was subcloned into the BamHI site of pUC18 producing pCGN709. The EcoRI-SmaI polylinker region of pCGN709 was substituted with the EcoRI-SmaI fragment of pCGN587, which contains the kanamycin resistance gene (APH3-II) producing pCGN726.

The EcoRI-SalI fragment of pCGN726 plus the BglII-EcoRI fragment of pCGN734 were inserted into the BamHI-SalI site of pUC8-Cm producing pCGN738. pCGN726c is derived from pCGN738 by deleting the 900 bp EcoRI-EcoRI fragment.

To construct pCGN167, the AluI fragment of CaMV (bp 7144-7735) (Gardner et al., *Nucl. Acid Res.* (1981) 9:2871-2888) was obtained by digestion with AluI and cloned into the HincII site of M13mp7 (Messing et al., *Nucl. Acids Res.* (1981) 9:309-321) to create C614. An EcoRI digest of C614 produced the EcoRI fragment from C614 containing the 35S promoter which was cloned into the EcoRI site of pUC8 (Vieira and Messing, *Gene* (1982) 19:259) to produce pCGN146.

To trim the promoter region, the BglII site (bp 7670) was treated with BglII and resected with Bal31 and subsequently a BglII linker was attached to the Bal31 treated DNA to produce pCGN147.

pCGN148a containing a promoter region, selectable marker (KAN with 2 ATG's) and 3' region, was prepared by digesting pCGN528 with BglII and inserting the BamHI-BglII promoter fragment from pCGN147. This fragment was cloned into the BglII site of pCGN528 so that the BglII site was proximal to the kanamycin gene of pCGN528.

The shuttle vector used for this construct, pCGN528, was made as follows. pCGN525 was made by digesting a plasmid containing Tn5 which harbors a kanamycin gene (Jorgenson et al., *Mol. Gen. Genet.* (1979) 177:65) with HindIII-BamHI and inserting the HindIII-BamHI fragment containing the kanamycin gene into the HindIII-BamHI sites in the tetracycline gene of pACYC184 (Chang and Cohen, *J. Bacteriol.* (1978) 134: 1141–1156). pCGN526 was made by inserting the BamHI fragment 19 of pTiA6 (Thomashow et al., *Cell* (1980) 19:729–739), modified with XhoI linkers inserted into the SmaI site, into the BamHI site of pCGN525. pCGN528 was obtained by deleting the small XhoI fragment from pCGN526 by digesting with XhoI and religating.

pCGN149a was made by cloning the BamNI-kanamycin gene fragment from pMB9KanXXI into the BamHI site of pCGN148a.

pMB9KanXXI is a pUC4K variant (Vieira and Messing, *Gene* (1982) 19:259–268) which has the XhoI site missing but contains a functional kanamycin gene from Tn903 to allow for efficient selection in Arobacterium.

pCGN149a was digested with BglII and SphI. This small BglII-SphI fragment of pCGN149a was replaced with the BamHI-SphI fragment from MI (see below) isolated by digestion with BamHI and SphI. This produces pCGN167, a construct containing a full length CaMV promoter, 1ATG-kanamycin gene, 3' end and the bacterial Tn903-type kanamycin gene. MI is an EcoRI fragment from pCGN546X (see construction of pCGN587) and was cloned into the EcoRI cloning site of M13mp9 in such a way that the PstI site in the 1ATG-kanamycin gene was proximal to the polylinker region of M13mp9.

The HindIII-BamHI fragment in the pCGN167 containing the CaMV-35S promoter, 1ATG-kanamycin gene and the BamHI-fragment 19 of pTiA6 was cloned into the BamHI-HindIII sites of pUC19 creating pCGN976. The 35S promoter and 3' region from transcript 7 was developed by inserting a 0.7 kb HindIII-EcoRI fragment of pCGN976 (35S promoter) and the 0.5 kb EcoRI-SalI fragment of pCGN709 (transcript 7:3') into the HindIII-SalI sites of pCGN566 creating pCGN766c.

The 0.7 kb HindIII-EcoRI fragment of pCGN766c (CaMV-35S promoter) was ligated to the 1.5 kb EcoRI-SalI fragment in pCGN726c (1ATG-KAN 3' region) followed by insertion into the HindIII-SalI sites of pUC119 to produce pCGN778. The 2.2 kb region of pCGN778, HindIII-SalI fragment containing the CaMV-35S promoter and 1ATG-KAN-3' region was used to replace the HindIII-SalI linker region of pCGN739 to produce pCGN783.

Transfer of the Binary Vector pCGN948 into Arobacterium pCGN948 was introduced into Arobacterium tumefaciens EHA101 (Hood et al., *J. Bacteriol.* (1986) 168:1291–1301) by transformation. An overnight 2 ml culture of EHA101 was grown in MG/L broth at 30° C. 0.5 ml was inoculated into 100 ml of MG/L broth (Garfinkel and Nester, *J. Bacteriol.* (1980) 144:732–743) and grown in a shaking incubator for 5 h at 30° C. The cells were pelleted by centrifugation at 7K, resuspended in 1 ml of MG/L broth and placed on ice. Approximately, 1 $\mu$g of pCGN948 DNA was placed in 100 $\mu$l of MG/L broth to which 200 $\mu$l of the EHA101 suspension was added; the tube containing the DNA-cell mix was immediately placed into a dry ice/ethanol bath for 5 minutes. The tube was quick thawed by 5 minutes in 37° C. water bath followed by 2 h of shaking at 30° C. after adding 1 ml of fresh MG/L medium. The cells were pelleted and spread onto MG/L plates (1.5% agar) containing 100 mg/1 gentamicin. Plasmid DNA was isolated from individual gentamicin-resistant colonies, transformed back into *E. coli*, and characterized by restriction enzyme analysis to verify that the gentamicin-resistant EHA101 contained intact copies of pCGN948. Single colonies are picked and purified by two more streakings on MG/L plates containing 100 mg/1 gentamicin.

Transformation and Regeneration of *B. Napus*

Seeds of *Brassica napus* cv Westar were soaked in 95% ethanol for 4 minutes. They were sterilized in 1% solution of sodium hypochlorite with 50 $\mu$l "Tween 20" surfactant per 100 ml sterile solution. After soaking for 45 minutes, seeds were rinsed 4 times with sterile distilled water. They were planted in sterile plastic boxes 7 cm wide, 7 cm long, and 10 cm high (Magenta) containing 50 ml of 1/10th concentration of MS (Murashige minimal organics medium, Gibco) with added pyridoxine (50 $\mu$g/1), nicotinic acid (50 g/1), glycine (200 $\mu$g/1) and solidified with 0.6% agar. The seeds germinated and were grown at 22° C. in a 16h-8h light-dark cycle with light intensity approximately 65 $\mu Em^{31}\ 2S^{31}\ 1$. After 5 days the seedlings were taken under sterile conditions and the hypocotyls excised and cut into pieces of about 4 mm in length. The hypocotyl segments were placed on a feeder plate or without the feeder layer on top of a filter paper on the solidified B5 0/1/1 or B5 0/1/0 medium. B5 0/1/0 medium contains B5 salts and vitamins (Gamborg, Miller and Ojima, *Experimental Cell Res.* (1968) 50:151–158), 3% sucrose, 2,4-dichlorophenoxyacetic acid (1.0 mg/1), pH adjusted to 5.8, and the medium is solidified with 0.6% Phytagar; B5 0/1/1 is the same with the addition of 1.0 mg/1 kinetin. Feeder plates were prepared 24 hours in advance by pipetting 1.0 ml of a stationary phase tobacco suspension culture (maintained as described in Fillatti et al., *Molecular General Genetics* (1987) 206:192–199) onto B5 0/1/0 or B5 0/1/1 medium. Hypocotyl segments were cut and placed on feeder plates 24 hours prior to Arobacterium treatment.

*Arobacterium tumefaciens* (strain EHA101×948) was prepared by incubating a single colony of Arobacterium in MG/L broth at 30° C. Bacteria were harvested 16 hours later and dilutions of $10^8$ bacteria per ml were prepared in MG/L broth. Hypocotyl segments were inoculated with bacteria by placing the segments in an Agrobacterium suspension and allowing them to sit for 30–60 minutes, then removing and transferring to Petri plates containing B5 0/1/1 or 0/1/0 medium (0/1/1 intends 1 mg/l 2,4-D and 1 mg/l kinetin and 0/1/0 intends no kinetin). The plates were incubated in low light at 22° C. The co-incubation of bacteria with the hypocotyl segments took place for 24-48 hours. The hypocotyl segments were removed and placed on B5 0/1/1 or 0/1/0 containing 500 mg/l carbenicillin (kanamycin sulfate at 10, 25, or 50 mg/l was sometimes added at this time) for 7 days in continuous light (approximately 65 $\mu Em^{31}\, 2S^{-1}$) at 22° C. The segments were transferred to B5 salts medium containing 1% sucrose, 3 mg/l benzylamino purine (BAP) and 1 mg/l zeatin. This was supplemented with 500 mg/l carbenicillin, 10, 25, or 50 mg/l kanamycin sulfate, and solidified with 0.6% Phy. tagar (Gibco). Thereafter, explants were transferred to fresh medium every two weeks.

After one month green shoots developed from green calli which were selected on media containing kanamycin. Shoots continued to develop for three months. The shoots were cut from the calli when they were at least 1 cm high and placed on B5 medium with 1% sucrose, no added growth substances, 300 mg/l carbenicillin, and solidified with 0.6% phytagar. The shoots continued to grow and several leaves were removed to test for neomycin phosphotransferase II (NPTII) activity. Shoots which were positive for NPTII activity were placed in Magenta boxes containing B5 0/1/1 medium with 1% sucrose, 2 mg/l indolebutyric acid, 200 mg/l carbenicillin, and solidified with 0.6% Phytagar. After a few weeks the shoots developed roots and were transferred to soil. The plants were grown in a growth chamber at 22° C. in a 16–8 hours light-dark cycle with light intensity 220 $\mu Em^{31}\, 2S^{31}\, 1$ and after several weeks were transferred to the greenhouse.

Southern Data

Regenerated *B. napus* plants from cocultivations of *Arobacterium tumefaciens* EHA101 containing pCGN948 and *B. napus* hypocotyls were examined for proper integration and embyro-specific expression of the spinach leaf ACP gene. Southern analysis was performed using DNA isolated from leaves of regenerated plants by the method of Dellaporta et al. (*Plant Mol. Biol. Rep.* (1983) 1:19-21) and purified once by banding in CsCl. DNA (10 $\mu g$) was digested with the restriction enzyme EcoRI, electrophoresed on a 0.7% agarose gel and blotted to nitrocellulose (see Maniatis et al., (1982) supra.). Blots were probed with pCGN945 DNA containing 1.8 kb of the spinach ACP sequence or with the EcoRI-HindIII fragment isolated from pCGN936c (made by transferring the HindIII-EcoRI fragment of pCGN930 into pCGN566) containing the napin5' sequences labeled with $^{32}P$-dCTP by nick translation (described by the manufacturer, BRL Nick Translation Reagent Kit, Bethesda Research Laboratories, Gaithersburg, Md.). Blots were prehybridized and hybridized in 50% formamide, 10X Denhardt's, 5XSSC, 0.1% SDS, 5 mM EDTA, 100 $\mu g/ml$ calf thymus DNA and 10% dextran sulfate (hybridization only) at 42° C. (Reagents described in Maniatis et al., (1982) supra.) Washes were in 1XSSC, 0.1% SDS, 30 min and twice in 0.1XSSC, 0.1% SDS 15 min each at 55° C.

Autoradiograms showed two bands of approximately 3.3 and 3.2 kb hybridize in the EcoRI digests of DNA from four plants when probed with the ACP gene (pCGN945) indicating proper integration of the spinach leaf ACP construct in the plant genome since 3.3 and 3.2 kb EcoRI fragments are present in the T-DNA region of pCGN948. The gene construct was present in single or multiple loci in the different plants as judged by the number of plant DNA-construct DNA border fragments detected when probed with the napin 5' sequences.

Northern Data

Expression of the integrated spinach leaf ACP gene from the napin promoter was detected by Northern analysis in seeds but not leaves of one of the transformed plants shown to contain the construct DNA. Developing seeds were collected from the transformed plant 21 days postanthesis. Embryos were dissected from the seeds and frozen in liquid nitrogen. Total RNA was isolated from the seed embryos and from leaves of the transformed plant by the method of Crouch et al., (1983) supra, electrophoresed on formaldehyde-containing 1.5% agarose gels as described (Shewmaker et al., Virology (1985) 140:281-288) and blotted to nitrocellulose (Thomas, Proc. Natl. Acad. Sci. USA (1980) 77:5201-5205). Blots were prehybridized, hybridized, and washed as described above. The probe was an isolated PstI-BamHI fragment from pCGN945 containing only spinach leaf ACP sequences labeled by nick translation.

An RNA band of $\sim 0.8$ kb was detected in embryos but not leaves of the transformed plant indicating seed-specific expression of the spinach leaf ACP gene.

Example II

Construction of B. Campestris Napin Promoter Cassette

A BglII partial genomic library of B. campestris DNA was made in the lambda vector Charon 35 using established protocols (Maniatis et al., (1982) supra). The titer of the amplified library was $\sim 1.2 \times 10^9$ phage/ml. Four hundred thousand recombinant bacteriophage were plated at a density of $10^5$ per 9$\times$9 in NZY plate (NZYM as described in Maniatis et al., (1982)supra) in NZY+10 mM MgSO$_4$+0.9% agarose after adsorption to DH1 *E. coli* cells (Hanahan, *Mol. Biol.* (1983) 166:557) for 20 main at 37° C. Plates were incubated at 37° C. for $\sim 13$ hours, cooled at 4° C. for 2.5 hours and the phage were lifted onto Gene Screen Plus (New England Nuclear) by laying precut filters over the plates for approximately 1 min and peeling them off. The adsorbed phage DNA was immobilized by floating the filter on 1.5M NaCl, 0.5M NaOH for 1 min., neutralizing in 1.5M NaCl, 0.5M Tris-HCl, pH 8.0 for 2 rain and 2XSSC for 3 min. Filters were air dried until just damp, prehybridized and hybridized at 42° C. as described for Southern analysis. Filters were probed for napin-containing clones using an XhoI-SalI fragment of the cDNA clone BE5 which was isolated from the *B. campestris* seed cDNA library described using the probe pN1 (Crouch et al., (1983) supra). Three plaques were hybridized strongly on duplicate filters and were plaque purified as described (Maniatis et al., (1982) supra).

One of the clones named lambda CGN1-2 was restriction mapped and the napin gene was localized to overlapping 2.7 kb XhoI and 2.1 kb SalI restriction fragments. The two fragments were subcloned from lambda CGN1-2 DNA into pCGN789 (a pUC based vector the same as pUC119 with the normal polylinker replaced by the synthetic linker —5' GGAATTCGT-CGACAGATCTCTGCAG CTCGAGGGATC-CAAGCTT 3'(which represents the polylinker EcoRI, SalI, BglII, PstI, XhoI, BamHI, HindIII). The identity of the subclones as napin was confirmed by sequencing. The entire coding region sequence as well as extensive 5' upstream and 3' downstream sequences were determined (FIG. 2). The lambda CGN1-2 napin gene is that encoding the mRNA corresponding to the BE5 cDNA as determined by the exact match of their nucleotide sequences.

An expression cassette was constructed from the 5'-end and the 3'-end of the lambda CGN1-2 napin gene as follows in an analogous manner to the construction of pCGN944. The majority of the napin coding region of pCGN940 was deleted by digestion with SalI and religation to form pCGN1800. Single-stranded DNA from pCGN1800 was used in an in vitro mutagenesis reaction (Adelman et al., DNA (1983) 2:183–193) using the synthetic oligonucleotide 5' GCTTGTTCGCCATG-GATATCTT CTGTATGTTC 3'. This oligonucleotide inserted an EcoRV and an NcoI restriction site at the junction of the promoter region and the ATG start codon of the napin gene. An appropriate mutant was identified by hybridization to the oligonucleotide used for the mutagenesis and sequence analysis and named pCGN1801.

A 1.7 kb promoter fragment was subcloned from pCGN1801 by partial digestion with EcoRV and ligation to pCGN786 (a pCGN566 chloramphenicol based vector with the synthetic linker described above in place of the normal polylinker) cut with EcoRI and blunted by filling in with DNA Polymerase I Klenow fragment to create pCGN1802. 3' sequences from the lambda CGN1-2 napin gene were added to XhoI-HindIII digested pCGN1802 from pCGN941. digested with XhoI and HindIII. The resulting clone, pCGN1803, contains approximately 1.6 kb of napin 3'-sequences as well as promoter sequences, but a 326 nucleotide HindIII fragment normally found at the 3'-end of lambda CGN1-2 is inserted opposite to its natural orientation. As a result, there are two HindIII sites in pCGN1803. This reversed fragment was removed by digestion of pCGN1803 with HindIII. Following religation, a clone was selected which now contained only approximately 1.25 kb of the original 1.6 napin 3'-sequence. This clone, pCGN1808, is the lambda CGN1-2 expression cassette and contains 1.725 kb of napin promoter sequence, and 1.265 kb of napin 3' sequences with the Unique cloning sites SalI, BglI, PstI, and XhoI in between. Any sequence that requires seed-specific transcription or expression in Brassica, for example, a fatty acid gene, can be inserted in this cassette in a manner analogous to that described for spinach leaf ACP and the B. napus napin cassette (see Example I.)

Example III

Other seed-specific promoters may be isolated from genes encoding proteins involved in seed triacylglycerol synthesis, such as acyl carrier protein from Brassica seeds. Immature seed were collected from *Brassica campestris* cv. "R-500," a self-compatible variety of turnip rape. Whole seeds were collected at stages corresponding approximately to 14 to 28 days after flowering. RNA isolation and preparation of a cDNA bank was as described above for the isolation of a spinach ACP cDNA clone except the vector used was pCGN565. To probe the cDNA bank, the oligonucleotide (5')-ACTTTCTCAACTGTCTCTGGTTTAG-CAGC-(3') was synthesized using an Applied Biosystems DNA Synthesizer, model 380A, according to manufacturer's recommendations. This synthetic DNA molecule will hybridize at low stringencies to DNA or RNA sequences coding for the amino acid sequence (ala-ala-lys-pro-glu-thr-val-glu-lys-val).

This amino acid sequence has been reported for ACP isolated from seeds of *Brassica napus* (Slabas et al., 7th International Symposium of the Structure and Function of Plant Lipids, University of California, Davis, CA, 1986); ACP from *B. campestris* seed is highly homologous. Approximately 2200 different cDNA clones were analyzed using a colony hybridization technique (Taub and Thompson, *Anal. Biochem.* (1982) 126:222–230) and hybridization conditions corresponding to Wood et al. (*Proc. Natl. Acad. Sci.* (1985) 82:1585–1588). DNA sequence analysis of two cDNA clones showing obvious hybridization to the oligonucleotide probe indicated that one, designated pCGN1Bcs, indeed coded for an ACP-precursor protein by the considerable homology of the encoded amino acid sequence with ACP proteins described from *Brassica napus* (Slabas et al., 1980 supra). Similarly to Example II, the ACP cDNA clone, pCGN1Bcs, was used to isolate ACP genomic clones containing the regulatory information for expression of ACP during triacylglyceride synthesis in the seeds. DNA was isolated from *B. campestris* cv. R500 young leaves by the procedure of Scofield and Crouch (*J. Biol. Chem.* (1987) 262: 12202–12208). A Sau3A partial genomic library of the *B. campestris* DNA was made in the lambda vector Embl 3 (Stratagene, San Diego, Calif.) using established protocols (Maniatis et al., (1982) supra) and manufacturer's instructions. The titer of the library was $\sim 1.0 \times 10^8$ phage/ml. Six hundred thousand recombinant bacteriophage were plated and screened as described in Example II with Ithe exception that the *E. coli* host cells used were strain P2392 (Stratagene, San Diego, Calif.). Filters were prehybridized and hybridized at 42° C. in 25 ml each of hybridization buffer containing 50% formamide, 10× Denhardt's, 5×SSC, 5 mM EDTA, 0.1% SDS, and 100 μg/ml denatured salmon sperm DNA (reagents described in Maniatis et al., (1982) supra). The probe used in these hybridizations was 0.2 μg of a nick-translated 530 base pair BglII-DraI fragment of pCGN1Bcs, the *B. campestris* ACP cDNA clone described above. Six plaques were hybridized strongly on duplicate filters after washing the filters at 55° C. in 0.1×SSC/0.2% SDS, and were plaque-purified as described (Maniatis et al., (1982) supra).

Figure 3B:
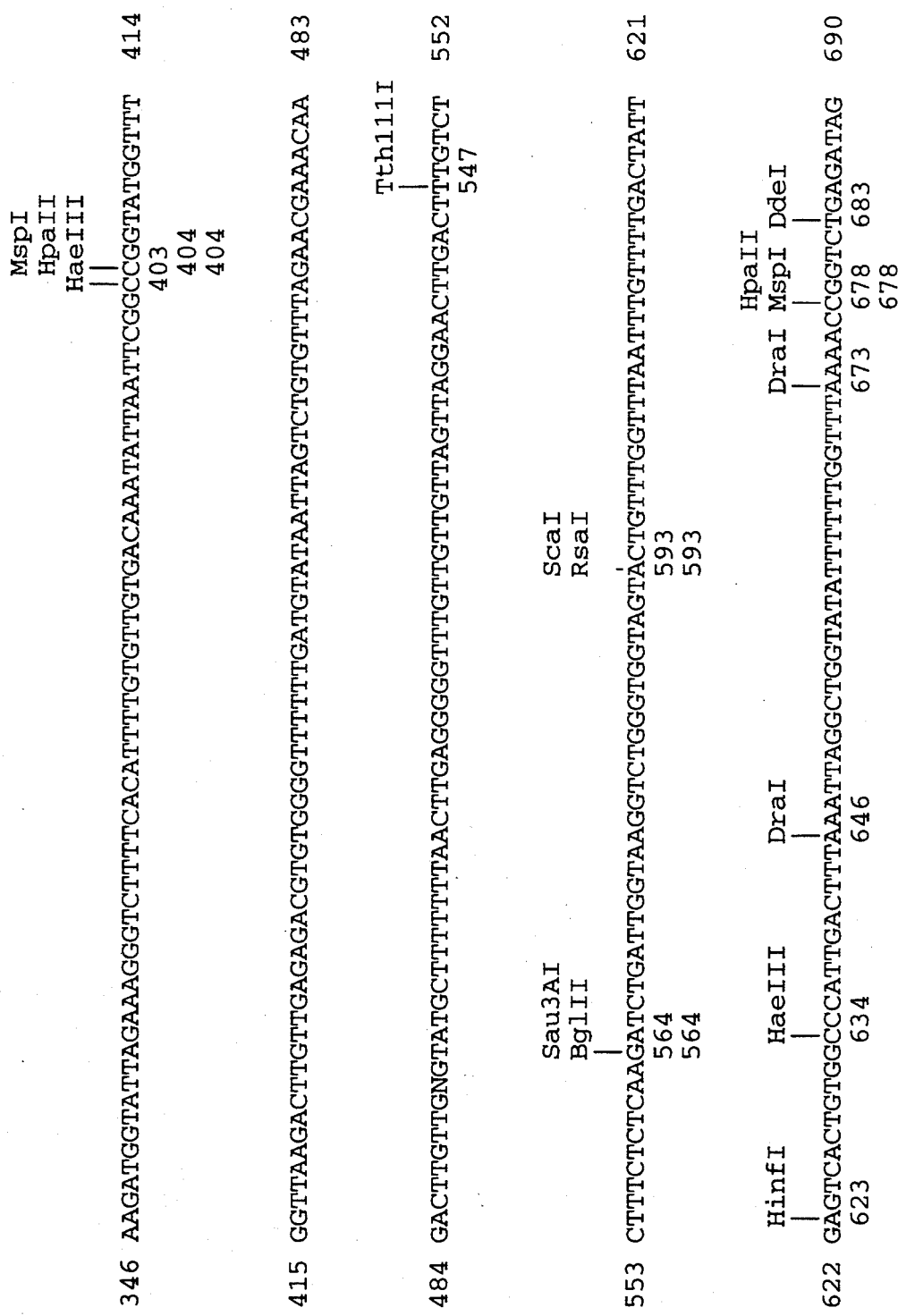
FIG. 3 is a partial nucleotide sequence of genomic ACP clone Bcg4-4. The coding region is indicated by the three-letter amino acid codes. Breaks in the coding region sequence represent introns. The underlined nucleotide at position 310 is ambiguous without further sequence analysis for confirmation.
Figure 3C:
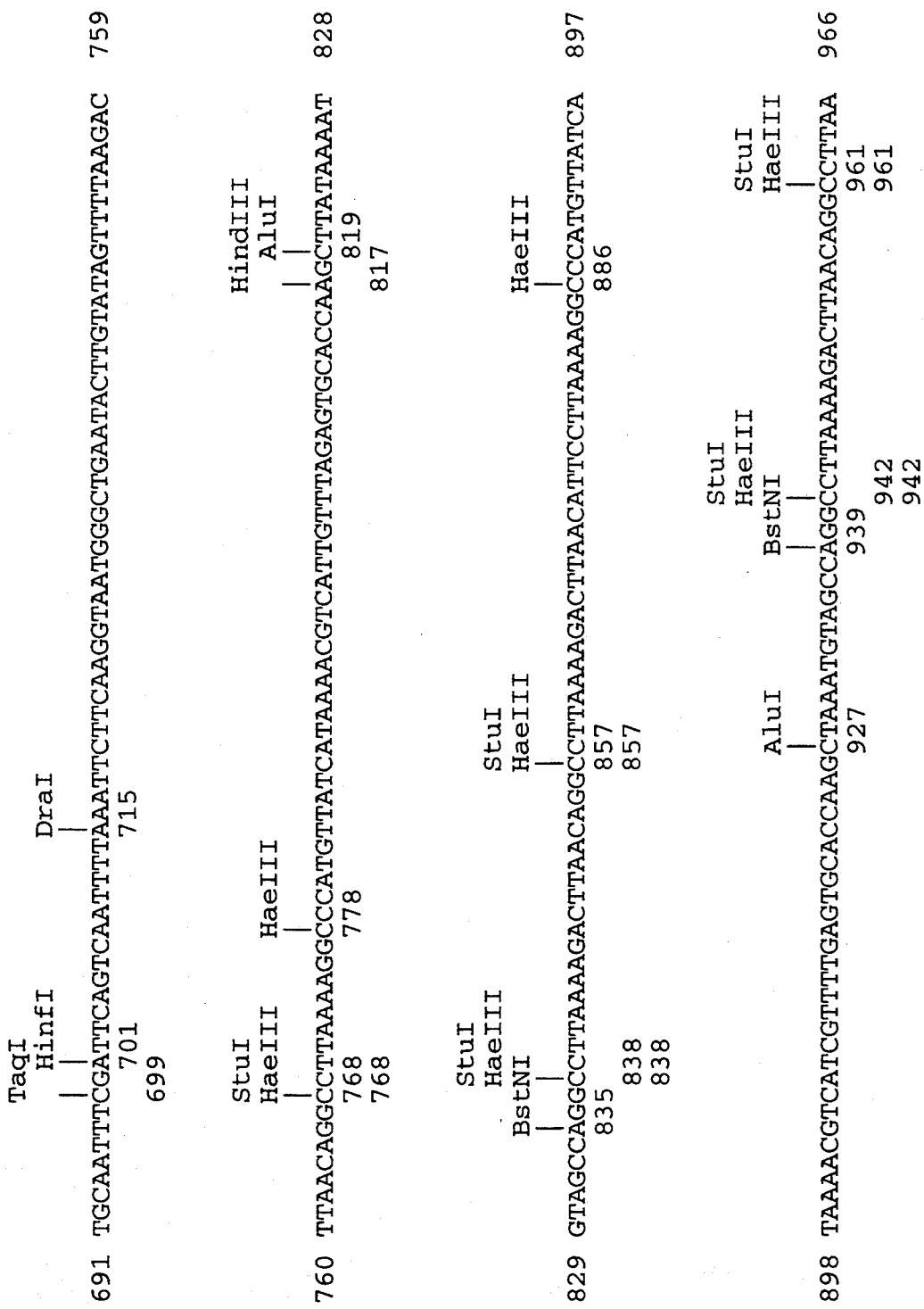

Restriction analysis followed by Southern hybridization was performed on some of the clones using the hybridization conditions and radiolabeled probe described above. One clone, Bcg4-4, contains the ACP gene on two overlapping restriction fragments, an $\sim 5.1$ kb SstI fragment and an $\sim 1.2$ kb HindIII fragment. These restriction fragments were subcloned into the cloning vector pCGN565. The DNA sequence of some regions of the subclones verified by homology that Bcg4-4 is an ACP gene. The sequence also shows that this particular ACP gene is expressed in plants, as the sequence in the coding region matches exactly the sequence of the pCGN1 Bcs ACP cDNA except for three regions. These regions are believed to be intervening sequences, a common element of eukaryotic genes that is spliced out during processing of mRNA (Padgett et al., *Ann. Rev. Biochem.* (1986) 55:1119–1150). Further restriction mapping of the SstI subclone identified an XhoI fragment containing $\sim 1.5$ kb of 5' sequence upstream from the XhoI site near the 5' end of the pCGN1 Bcs cDNA clone. This XhoI fragment was subcloned in opposite orientations in the cloning/sequencing vector Bluescript +(Stratagene, San Diego, Calif.) and the clones were designated pCGN1941 and pCGN1941'. DNA sequencing of 1 kb of the DNA upstream of the coding region was completed. Also, the complete sequence of the 1.2 kb HindIII subclone described above was determined. The DNA sequence derived from the clones described above is shown in FIG. 3. Additional sequences at the 3' end of the ACP gene were subcloned on an ~1.6 kb SstI-BglII fragment into Bluescript+ and Bluescript— (clones are designated pCGN1940 and pCGN1940'). The SstI site in these clones is the one found at the 3' end of the ACP coding region of pCGN1Bcs.

An expression cassette can be constructed from the 5' upstream sequences and 3' downstream sequences of Bcg4-4 as follows. The pCGN1941 XhoI subclone is used for the 5' regulatory region. This clone contains the XhoI insert in the opposite orientation of the lacZ gene. The 3' regulatory region is altered to allow cloning as a PstI-BglII fragment into pCGN565 by oligonucleotide site-directed mutagenesis. Single-stranded DNA is made from pCGN1940 and altered by mutagenesis as described (Adelman et al., supra) with the synthetic oligonucleotide 5'CTTAAGAAG-TAACCCGGGCTGCAGTTTTAGTATTAAGAG 3'. This oligonucleotide provides SmaI and PstI restriction sites just after the TAA stop codon of the pCGN1Bcs cDNA. The PstI-BglII 3' fragment is then cloned into the PstI and BamHI sites (the BamHI restriction site is destroyed in this process) of pCGN565. The resulting clone is digested with PstI and SmaI, and the fragment inserted into the corresponding sites in pCGN1941 (described above) in the same orientation as the 5' region. The resulting clone comprises the ACP expression cassette with PstI, ECoRI, and EcoRII sites available between the 5' and 3' regulatory regions for the cloning of genes to be expressed under the regulation of these ACP gene regions.

Example IV

Isolation of Seed-specific cDNA Clone, EA9

Ninety-six clones from the 14–28 day postanthesis B. campestris seed cDNA library (described in the previous example) were screened by dot blot hybridization of miniprep DNA on Gene Screen Plus nylon filters (NEN Research Products, Boston, Mass.). The probes used were radioactively labeled first-strand synthesis cDNAs made from the day 14–28 postanthesis seed mRNA or from B. campestris leaf mRNA. Clones which hybridized strongly to seed cDNA and little or not at all to leaf cDNA were catalogued. A number of clones were identified as representing the seed storage protein napin by cross-hybridization with an XhoI-SalI fragment of pNI (Crouch et al., (1983) supra), a B. napus napin cDNA. One of these napin clones, BE5, was used in Example II to identify a B. campestris genomic clone as a source of an embryo-specific promoter.

Another abundant class of cDNA clones were those represented by a clone designated EA9. EA9 cross-hybridized to seven other cDNA clones of 600 cDNAs screened by dot blot hybridization and was highly expressed in seeds and not in leaves. Northern blot analysis of mRNA isolated from day 14 postanthesis whole seed, and day 21 and 28 postanthesis embryos using a 700 bp EcoRI fragment of EA9 (see below) as a probe shows that EA9 is highly expressed at day 14 and expressed at a much lower level at day 21 and day 28 postanthesis. Because the embryo is so small at day 14, it was suspected that the predominant expression of EA9 might be in a tissue other than the embryo. Total RNA was isolated (Crouch et al., (1983) supra) from whole seed (14, 15, 17 and 19 days postanthesis), seed coats (day 14 and day 21 postanthesis) and embryos (day 21 postanthesis). Twenty-five μg of each sample were analyzed by Northern blot analysis as described in Example I. The probe used was a 0.7 kb ECoRI DNA fragment isolated from the EA9 cDNA and labeled by nicktranslation. The results of the Northern analysis showed the EA9 RNA was detected in whole seed at all times tested and in seed coats, but not in the embryo. A separate Northern analysis of whole seed RNA from days 13 through day 31 postanthesis (in two day intervals) indicated that EA9 was highly expressed between days 13 to 21 but was barely detectable by day 27 postanthesis.

In Situ Hybridization

Seed-coat specific expression of EA9 was confirmed by in situ hybridization analysis. Day 14 and 21 postanthesis whole seeds of B. campestris were fixed in a 4% paraformaldehyde phosphate buffered saline (PBS) solution. The tissue was then dehydrated through a graded tertiary-butyl alcohol (TBA) series, infiltrated with paraplast and cast into paraffin blocks for sectioning (Berlyn and Miksche, Botanical Microtechnique and Cytochemistry. (1976), Iowa State University Press). Five μm longitudinal sections of the embedded seeds (one cell-layer thickness) were generated on a Reichert Histostat rotary microtome. The paraffin ribbons containing the seed sections were then affixed to gelatin-chrome alum subbed slides (Berlyn and Miksche, (1976) supra).

Single-stranded radiolabeled RNA probes were made using the Riboprobe reaction system (Promega, Madison, Wis.). This system utilizes a vector which is derived from pUC12 and contains a bacteriophage SP6 promoter which lies immediately upstream from an M13 polylinker. First, the 700 bp EcoRI fragment was isolated from EA9 and subcloned into the polylinker region of the riboprobe vector in both orientations (sense and anti-sense). To generate a template for the transcription run-off transcription reactions, the recombinant plasmids were propagated, purified, and linearized with HindIII. The templates were then incubated in a reaction mixture containing the SP6 RNA polymerase, triphosphates and $^{35}$S-UTP (as described by the manufacturer). After adding RQ DNase (Promega), the labeled RNAs were run over Boehringer pre-packed Sephadex spin columns to remove unincorporated triphosphates.

The slides containing the sectioned seeds were hybridized with the radiolabeled sense and anti-sense RNA transcripts of EA9 according to the methods of Singer et al. (Biotechniques (1986) 4:230–241) and Taylor and Martineau (Plant. Physiol. (1986) 82:613–618). The hybridized slides were then treated with nuclear track emulsion NTB-3, (Eastman Kodak Company, Kodak Materials for Light Microscope Autoradiography, 1986) sealed in a light-tight box and exposed for 4 weeks at 5°–10° C. After bringing the slides to room temperature they were developed in D-19 developer (Eastman Kodak Company), rinsed, fixed and dehydrated through a graded alcohol series. Cover slips were mounted with cytoseal (VWR Scientific).

Hybridization of the radiolabeled anti-sense EA9 riboprobe was seen only in the seed coat tissue of both day 14 and 21 seeds. No hybridization of the radiolabeled sense EA9 riboprobe was seen in any seed tissues.

DNA Sequence and Gene Copy Number

Figure 4B:
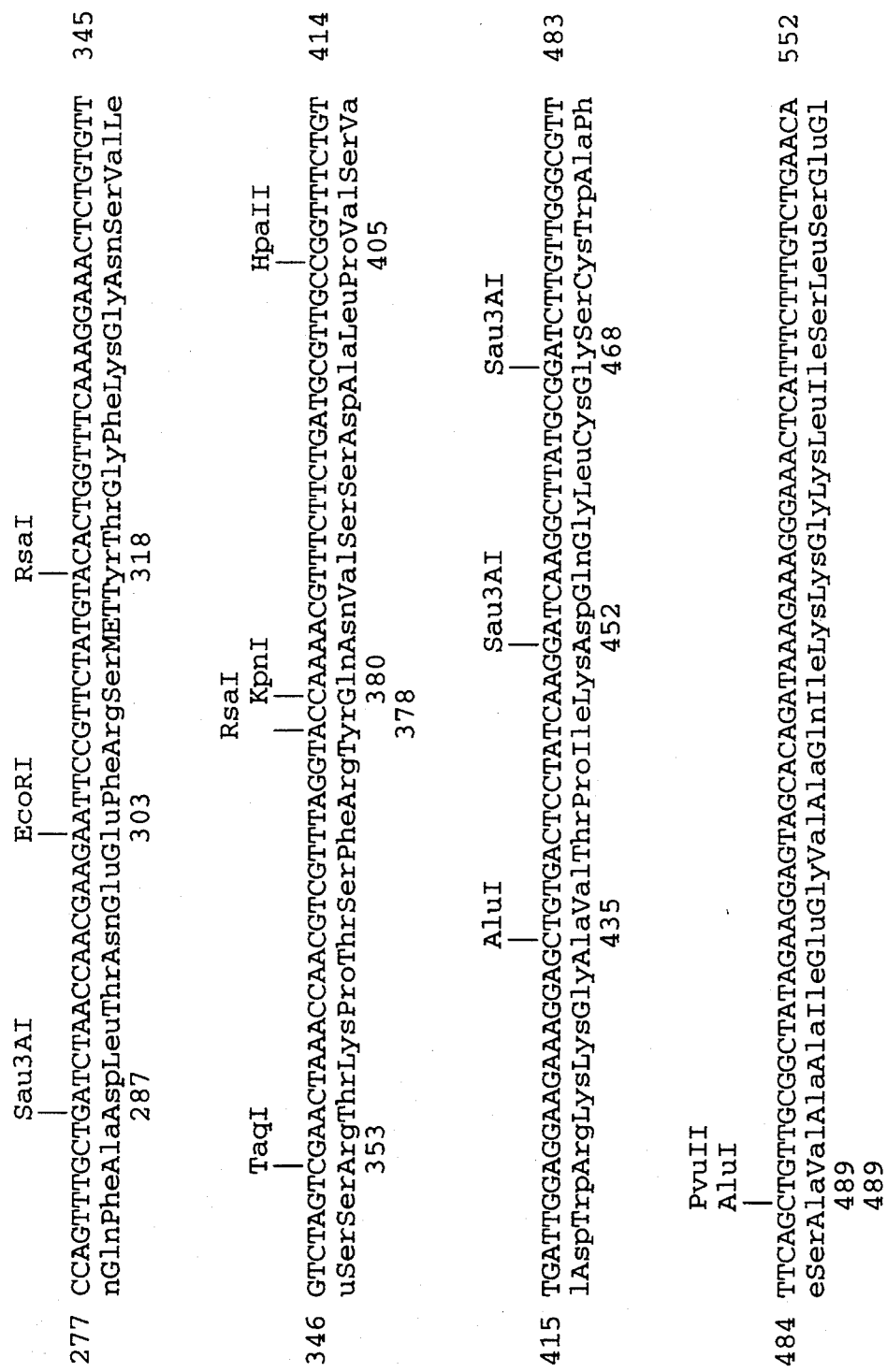
FIG. 4 is the complete nucleotide sequence of *B. campestris* cDNA EA9. The longest open reading frame is designated by the three letter amino acid code. PolyA tails are evident at the end of the sequence and a potential polyadenylation signal is underlined.

The restriction map and sequence of the EA9 cDNA clone have been determined (FIG. 4). Identification of a polyadenylation signal (Proudfoot and Brownlee, *Nature* (1976) 263:211-214) and of polyA tails at the 3'-end of EA9 indicated the orientation of the cDNA clone and the direction of transcription of the mRNA. The function of the encoded protein is unknown at this time.

EA9 is a member of a small gene family as shown by Southern blot analysis. DNA was isolated from *B. campestris* leaves (as described in Example I, Southern analysis), digested with either BamHI, BglII or HindIII and probed with a labeled fragment of EA9. Three fragments of genomic DNA hybridized in both BamHI and BglII digests. Only 2 bands hybridized in the HindIII digest. The data suggests that the EA9 family comprises between one and three genes.

The sequence of EA9 is used to synthesize a probe which identifies a unique class of Brassica seed-specific genes from a genomic library in the manner described in Examples II and III. The regulatory sequences of these genes is used to construct an expression cassette similar to those described for the napin genes, with the EA9 construct directing seed coat specific expression of any gene inserted in it.

Other Examples

Other seed-specific genes may also serve as useful sources of promoters. cDNA clones of cruciferin, the other major seed storage protein of *B. napus*, have been identified (Simon et al., (1985) supra) and could be used to screen a genomic library for promoters.

Without knowning the specific functions, yet other cDNA clones can be classified as to their level of expression in seed tissues, their timing of expression (i.e., when postanthesis they are expressed) and their approximate representation (copy number) in the *B. campestris* genome. Clones fitting the criteria necessary for expressing genes related to fatty acid synthesis or other seed functions can be used to screen a genomic library for genomic clones which contain the 5' and 3' regulatory regions necessary for expression. The non-coding regulatory regions can be manipulated to make a tissue-specific expression cassette in the general manner described for other genes in previous examples.

It is evident from the above results, that transcription or expression can be obtained specifically in seeds, so as to permit the modulation of phenotype or change in properties of a product of seed. It is found that one can use transcriptional initiation regions associated with the transcription of sequences in seeds in conjunction with sequences other than the normal sequence to produce endogenous or exogenous proteins or modulate the transcription or expression of nuclei c acid sequences. In this manner, seeds can be used to produce novel products, to provide for improved protein compositions, to modify the distribution of fatty acid, and the like.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A DNA construct comprising: in the 5' to 3' direction of transcription, a transcriptional initiation region from a gene which encodes a product preferentially expressed in a plant seed cell as compared with other plant cells, a DNA sequence of interest other than the native coding sequence of said gene, and a transcriptional termination region, wherein said gene is a napin gene, an acyl carrier protein gene or an EA9 gene.

2. The DNA construct according to claim 2, further comprising a ribosome binding site immediately downstream of said transcriptional initiation region.

3. The DNA construct according to claim 2, wherein said DNA sequence of interest is an open reading frame encoding an amino acid sequence.

4. The DNA construct according to claim 2, wherein said DNA sequence of interest is complementary to a mRNA endogenous to a plant seed cell.

5. The DNA construct according to claim 1, wherein said transcriptional initiation region is from a gene expressed in a Brassica seed cell.

6. The DNA construct according to claim 1, wherein said transcriptional initiation region is obtainable from any one of the group consisting of DNA sequences as shown in FIG. 1, FIG. 2, FIG. 3 and FIG. 4.

7. The DNA construct according to claim 1, wherein said transcriptional termination region is native with the transcriptional initiation region.

8. An expression cassette comprising:
in the 5'-3' direction of transcription, a seed-specific transcriptional initiation region wherein said transcriptional initiation region is free from the native DNA sequence under the regulatory control of said initiation region, a cloning site, and a transcriptional termination region, wherein said transcriptional initiation region is from a napin gene, an acyl carrier protein gene or an EA9 gene.

9. An expression cassette comprising:
in the 5'-3' direction of transcription, a transcriptional initiation region and ribosome binding site from a gene expressed in a seed embryo or a seed coat cell or from a gene encoding a seed storage protein, a linker or polylinker having one or a plurality of restriction sites for insertion of a gene to be expressed under transcriptional control of said transcriptional initiation region, and a transcriptional termination region, wherein said transcriptional initiation region and said ribosome binding site are from a napin gene, an acyl carrier protein gene or an EA9 gene.

10. The expression cassette according to claim 9, wherein a DNA sequence of interest heterologous to the napin gene, an acyl carrier protein gene or an EA9 gene is inserted into at least one of said restriction sites.

11. A Brassica host plant cell comprising a DNA construct according to any one of claims 1-7.

* * * * *